(12) United States Patent
Chen

(10) Patent No.: US 9,352,006 B2
(45) Date of Patent: May 31, 2016

(54) METHODS AND COMPOSITIONS FOR TREATING TUMORS USING MYELOID DERIVED SUPPRESSOR CELLS

(75) Inventor: Shu-Hsia Chen, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 177 days.

(21) Appl. No.: 13/880,339

(22) PCT Filed: Oct. 20, 2011

(86) PCT No.: PCT/US2011/057129
§ 371 (c)(1),
(2), (4) Date: Dec. 17, 2013

(87) PCT Pub. No.: WO2012/054747
PCT Pub. Date: Apr. 26, 2012

(65) Prior Publication Data
US 2014/0086869 A1    Mar. 27, 2014

Related U.S. Application Data

(60) Provisional application No. 61/394,950, filed on Oct. 20, 2010.

(51) Int. Cl.
| | | |
|---|---|---|
| A61K 35/766 | (2015.01) | |
| A61K 35/15  | (2015.01) | |
| A61K 35/17  | (2015.01) | |
| A61K 35/76  | (2015.01) | |
| A61K 39/00  | (2006.01) | |
| A61K 45/06  | (2006.01) | |

(52) U.S. Cl.
CPC ............ *A61K 35/766* (2013.01); *A61K 35/15* (2013.01); *A61K 35/17* (2013.01); *A61K 35/76* (2013.01); *A61K 39/0011* (2013.01); *A61K 45/06* (2013.01)

(58) Field of Classification Search
None
See application file for complete search history.

(56) References Cited

U.S. PATENT DOCUMENTS

2007/0071723 A1    3/2007    Coffey et al.

OTHER PUBLICATIONS

Serafini et al., The Journal of Experimental Medicine, Nov. 27, 2006, 203(12): 2691-2702.*
International Preliminary Report on Patentability mailed May 2, 2013, which issued in corresponding International Application No. PCT/US2011/057129.
Gabrilovich et al., "Myeloid-derived suppressor cells as regulators of the immune system"; Nature Rev. Immunol (2009); 9(3); 162-174.
Ohno et al., "Cell-specific targeting of Sindbis virus vectors displaying IgG-binding domains of protein"; A. Nat. Biotechnol (1997); 15(8); 763-767; abstract.
Willmon et al., Vesicular stomatitis virus-induced immune suppressor cells generate antagonism between intratumoral oncolytic virus and cyclophosphamide Mol There ePub (2010); 140-149.
International Search Report mailed May 31, 2012, which issued in corresponding International Application No. PCT/US2011/057129.
Stockmann, et al., "Deletion of vascular endothelial growth factor in myeloid cells accelerates tumorigenesis", *Nature*, vol. 456, Dec. 11, 2008, 6 pages.
Office Action for Chinese Application No. 201180061634.2 issued Mar. 27, 2014 and English translation. 16 pages.

* cited by examiner

*Primary Examiner* — Nicole Kinsey White
(74) *Attorney, Agent, or Firm* — Fish & Richardson P.C.

(57) ABSTRACT

Compositions and methods for diagnosing and treating tumors using myeloid derived suppressor cells (MDSCs) are provided. More particularly, the compositions contain labeled MDSCs or MDSCs in combination with oncolytic viruses, nano-particles or other anti-tumor agents.

17 Claims, 24 Drawing Sheets

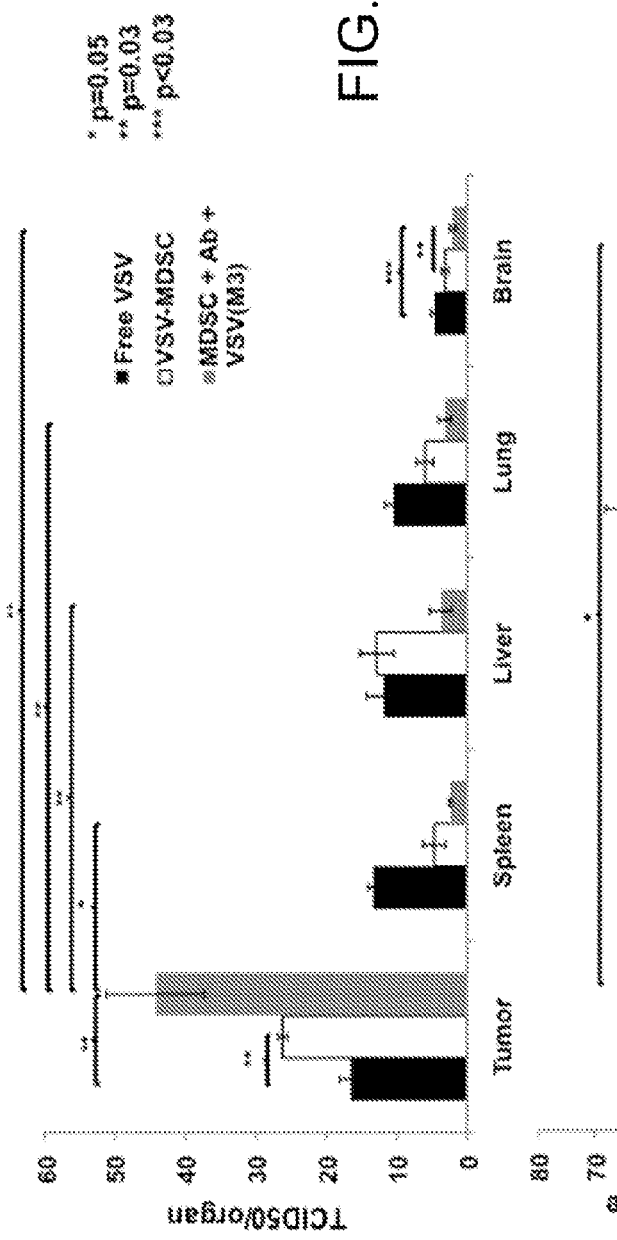
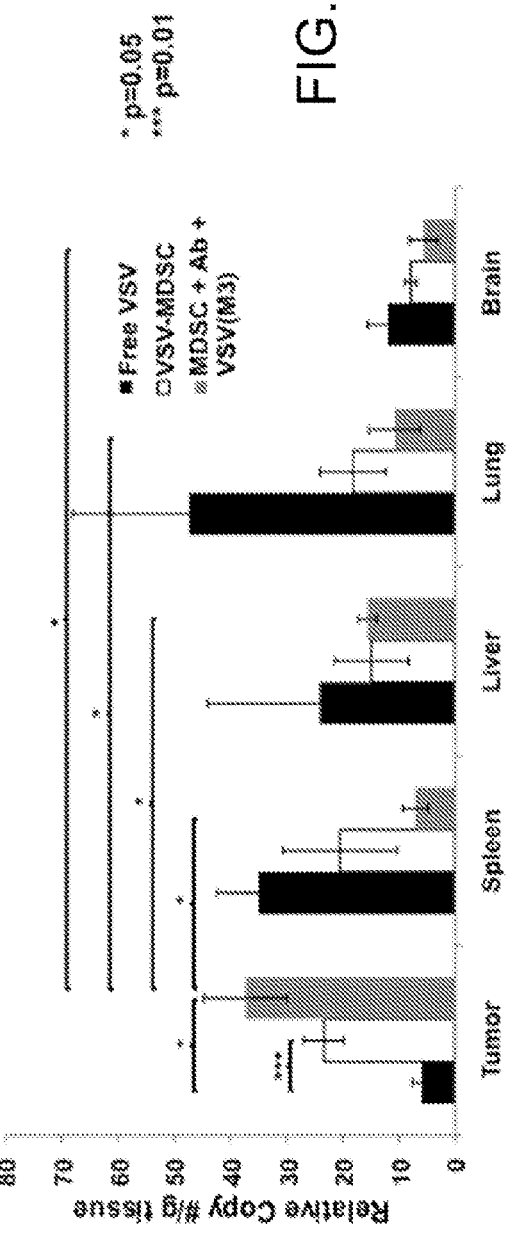
FIG. 10A
FIG. 10B

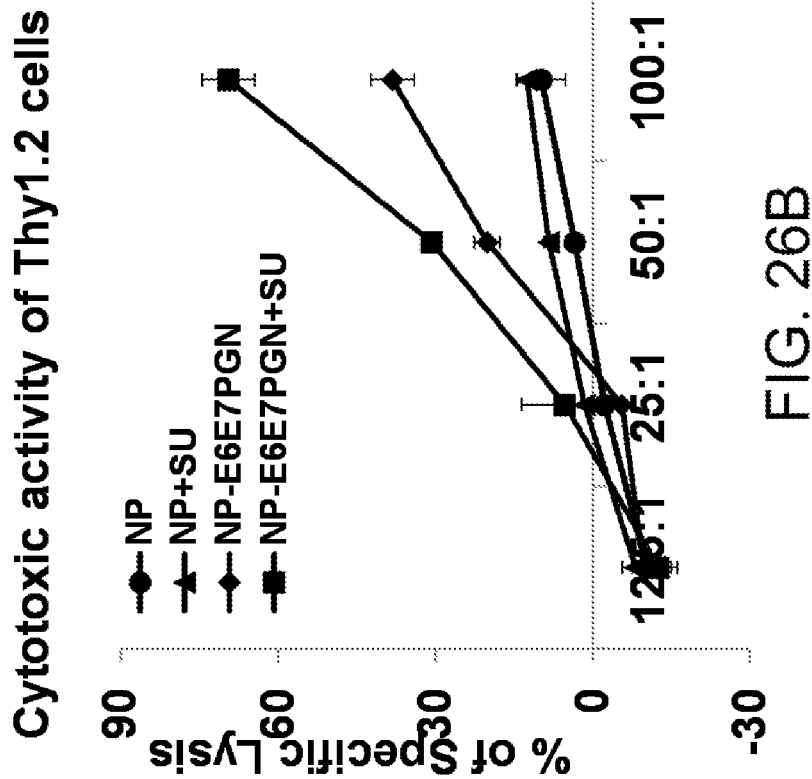
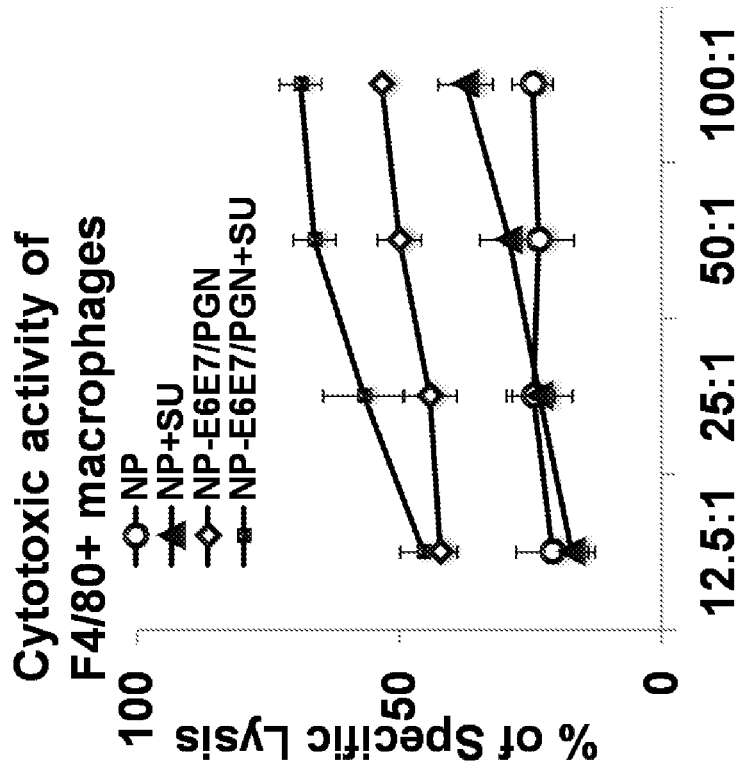
FIG. 26B
FIG. 26A

```
                         SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
ttcttggttc tccgagttgg                                                20

<210> SEQ ID NO 2
<211> LENGTH: 20
<212> TYPE: DNA
```

```
<213> ORGANISM: Artificial Sequence
<220> FEATURE:
<223> OTHER INFORMATION: Primer

<400> SEQUENCE: 2
aacaggagga tgcagcattt                                              20

<210> SEQ ID NO 3
<211> LENGTH: 10
<212> TYPE: PRT
<213> ORGANISM: human papilloma virus

<400> SEQUENCE: 3

Glu Val Tyr Asp Phe Ala Phe Arg Asp Leu
 1               5                  10

<210> SEQ ID NO 4
<211> LENGTH: 9
<212> TYPE: PRT
<213> ORGANISM: human papilloma virus

<400> SEQUENCE: 4

Arg Ala His Tyr Asn Ile Val Thr Phe
 1               5

<210> SEQ ID NO 5
<211> LENGTH: 4
<212> TYPE: RNA
<213> ORGANISM: human papilloma virus

<400> SEQUENCE: 5 uuau                                                                4
```

METHODS AND COMPOSITIONS FOR TREATING TUMORS USING MYELOID DERIVED SUPPRESSOR CELLS

RELATED APPLICATIONS

The present application is a U.S. National Phase application under 35 U.S.C. §371 of International Patent Application No. PCT/US2011/057129, filed Oct. 20, 2011, and claims the benefit of U.S. Provisional Patent Application No. 61/394,950, filed Oct. 20, 2010 both of which are incorporated by reference herein in their entirety. The International Application published in English on Apr. 26, 2012 as WO 2012/054747 under PCT Article 21(2).

REFERENCE TO SEQUENCE LISTING

Pursuant to 37 C.F.R. 1.821(c), a sequence listing is submitted herewith via EFS-Web as an ASCII compliant text file named "SequenceListing.txt" that was created on Oct. 10, 2011, and has a size of 1,086 bytes. The content of the aforementioned file named "SequenceListing.txt" is hereby incorporated by reference in its entirety.

FIELD OF THE INVENTION

This application relates to compositions and methods for diagnosing and treating tumors using myeloid derived suppressor cells (MDSCs).

BACKGROUND OF THE INVENTION

An oncolytic virus preferentially replicates in and lyses tumor cells while not exhibiting activity in non-transformed normal host cells. Several oncolytic viruses have been used in clinical trials with limited results due to limited replicative effect of oncolytic viruses and lack of an effective delivery system that specifically targets the metastatic tumor sites. Two commonly used oncolytic viruses include vesicular stomatitis virus (VSV) and adenovirus. VSV rapidly replicates and induces apoptosis in tumor cells, but not normal cells. The adenovirus, AdlTRAIL-EI, is a recombinant adenovirus with the viral replicative gene, EI, as well as the gene for tumor necrosis factor-related apoptosis-inducing ligand (TRAIL) driven by human telomerase reverse transcriptase promoter (hTERT). This virus has been shown to replicate only in cells in which telomerase is constitutively active (i.e., tumor cells) and has been shown safe and effective as an oncolytic virus in murine models.

The use of tumor targeting carriers has shown some promise in increasing tumoricidal effects of oncolytic viruses. Monocyte cell lines, T cells, and NKT cells have all been employed with limited success in attempts to find suitable tumor targeting carriers. It is possible to eliminate tumor cells from lymphoid organs when employing T cells as oncolytic carriers [see, Ilett et al. 2009 Gene Ther 16(5):689-99]. The effect obtained, however, was due to T cell tropism for lymphoid organs. This approach is therefore ineffective for targeting tumor cells in non-lymphoid organs. Creating genetically engineered T cells for tumor targeting would also be time consuming and labor intensive. Other candidate carriers for oncolytic viruses and other anti-tumor agents are therefore needed for the treatment of tumors, both in lymph nodes and in non-lymphoid organs.

SUMMARY OF THE INVENTION

The invention relates to compositions and methods for diagnosing and treating tumors using myeloid derived suppressor cells (MDSCs).

In certain embodiments, a composition comprising an isolated myeloid derived suppressor cell (MDSC) and an anti-tumor agent is provided. In some embodiments, the anti-tumor agent is an oncolytic virus. In other embodiments, the oncolytic virus is a member selected from the group consisting of vesicular stomatitis virus (VSV), rVSV(MΔ51)-M3 mutant VSV, AdlTRAIL-EI, ONYX-015, CV706, JX-584, CGTG-102, vaccinia virus, reovirus, and poliovirus.

In certain embodiments, a composition comprising an isolated MDSC and an anti-tumor agent is provided, wherein the anti-tumor agent is an oncolytic virus and the MDSC is infected with the oncolytic virus.

In certain embodiments, a composition comprising an isolated myeloid derived suppressor cell (MDSC) and an anti-tumor agent is provided, wherein the anti-tumor agent is a member selected from the group consisting of a chemotherapeutic agent, interferon-gamma, tumor necrosis factor (TNF)-alpha, TNF-beta, an antagonist of TGF-beta, an antagonist of IL-10, and an anti-angiogenic factor.

In a specific embodiment, a composition comprising an isolated myeloid derived suppressor cell (MDSC) and a vesicular stomatitis virus (VSV) is provided.

In one embodiment, a pharmaceutical formulation comprising a myeloid derived suppressor cell (MDSC), an anti-tumor agent, and a pharmaceutically acceptable carrier is provided. In certain embodiments, the pharmaceutical formulation is formulated for parenteral administration. In some embodiments, the anti-tumor agent in the pharmaceutical formulation is an oncolytic virus. In certain embodiments, the anti-tumor agent is at least one chemotherapeutic agent.

In one embodiment, a method for treating a tumor comprising administering to a patient in need of such treatment a therapeutically effective amount of a pharmaceutical formulation comprising an isolated myeloid derived suppressor cell (MDSC), an anti-tumor agent, and a pharmaceutical carrier is provided. In one embodiment, the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In certain embodiments, the patient is a mammal. In one embodiment, the mammal is a human.

In one embodiment, a method for treating a tumor comprising administering to a patient in need of such treatment an effective amount for treating the tumor of a composition comprising an isolated myeloid derived suppressor cell (MDSC) and an anti-tumor agent is provided. In certain embodiments, the patient is a mammal. In one embodiment, the mammal is a human.

In one embodiment, a method for treating a tumor comprising administering to a patient in need of such treatment an effective amount for treating the tumor of a composition comprising an isolated myeloid derived suppressor cell (MDSC) and an anti-tumor agent is provided, wherein the patient has a tumor selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

In one embodiment, a method for diagnosing a tumor in a subject is provided, which method comprises: (i) administering to the subject labeled myeloid derived suppressor cells (MDSCs); and (ii) determining whether said labeled MDSCs become concentrated in at least one site in said subject. In a specific embodiment, the method for diagnosing a tumor in a subject further comprises performing a PET scan on said subject to confirm the diagnosis of the tumor. In one embodiment, the MDSCs are labeled with ferumoxides. In another embodiment, the labeled MDSCs are detected in vivo using magnetic resonance imaging (MRI).

In one embodiment, a kit comprising an isolated myeloid derived suppressor cell (MDSC) and an anti-tumor agent is provided. In another embodiment, the anti-tumor agent in the kit is an oncolytic virus or chemotherapeutic agent.

In one embodiment, a kit comprising an isolated myeloid derived suppressor cell (MDSC) labeled with a marker that is detectable in vivo is provided. In another embodiment, the marker is ferumoxides.

In certain of the above embodiments, the MDSC expresses the cell surface markers CD11b and CD33. In some of the above embodiments, the MDSC also expresses at least one cell surface marker selected from the group consisting of CD14, CD15, CD16, and CD34.

In certain of the above embodiments, the MDSC expresses the cell surface markers CD11b, CD115, Gr1 and Ly6C.

In certain embodiments, the anti-tumor agent is a nanoparticle. In some embodiments, the nanoparticle is conjugated to at least one adjuvant and/or to at least one antigen. In a specific embodiment, the antigen is a tumor antigen. In another specific embodiment, the adjuvant is a Toll-like receptor (TLR) ligand adjuvant, such an adjuvant selected from the group consisting of lipopolysaccharide (LPS), peptidoglycan (PGN), CpG, PolyIC, monophosphoryl Lipid A, flagellin, and ssRNA with 6 UUAU (SEQ ID NO: 5) repeats, or combination thereof.

These and other embodiments of the present invention will be apparent to those of ordinary skill in the art in light of the present specification, claims and drawings.

BRIEF DESCRIPTION OF THE DRAWINGS

FIG. 10A is a bar graph showing the $TCID_{50}$ in the indicated site or organs (tumor, spleen, liver, lung, brain) of mice bearing intrahepatic MCA26 tumors and treated with free VSV, MDSCs passively loaded with VSV(M3) without anti-VSV-G antibody (VSV-MDSC), or MDSC+antiVSV-G antibody (Ab)+VSV(M3). Mice were sacrificed 96 hours after treatment and the tumor or organs were homogenized and assayed for $TCID_{50}$. FIG. 10B is a graph quantifying the relative viral copy number per gram (g) of tissue as determined by qRT-PCR. RNA was isolated and analyzed for VSV-G via qRT-PCR. Mice treated with MDSC+Ab+VSV (M3) demonstrated significantly more virus and viral RNA in the tumor than in other organs as well as demonstrating more virus and viral RNA in the tumor than in mice treated with VSV-MDSCs and free virus; in FIGS. 10A and 10B: *p=0.05, p=0.03, *p=0.01

FIG. 26A and FIG. 26B are line graphs quantifying cytotoxic activity of F4/80+ tumor macrophages purified (FIG. 26A), and Thy1.2 T cells (FIG. 26B) isolated from tumor infiltrating leukocytes (TIL) against TC-1 tumor cells. The groups from which the cells were isolated are as described above for FIG. 24.

DETAILED DESCRIPTION OF THE INVENTION

Figure 1:
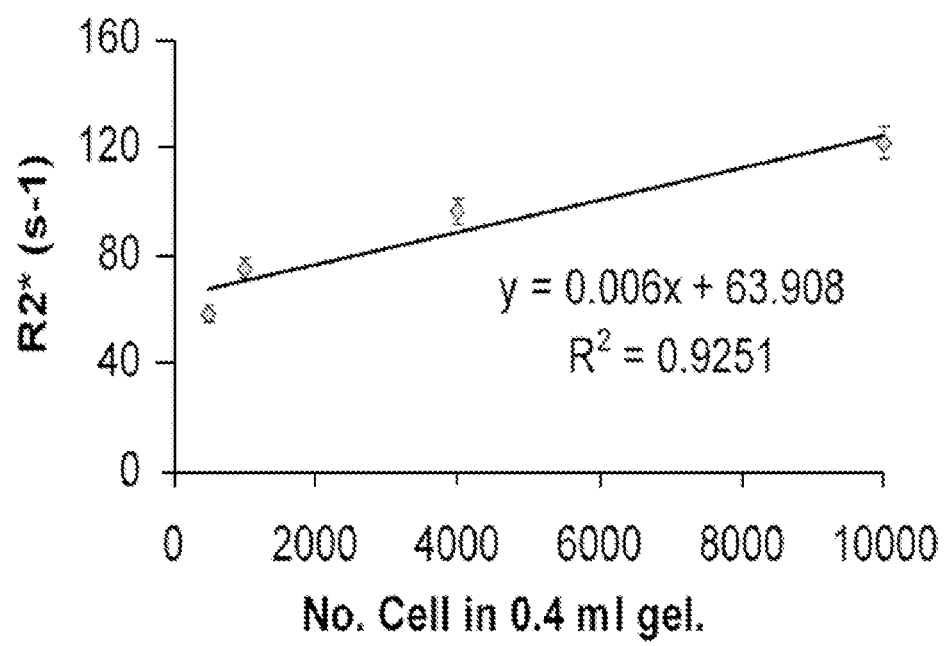
FIG. 1 is a standard curve showing effective ferumoxides labeling of MDSCs, as determined by MRI.

The present invention advantageously provides approaches for diagnosing and treating tumors, and is based in part on the discovery that, in multiple cancer models, e.g., metastatic colon, hepatic, cervical and melanoma cancer models, MDSCs preferentially migrated to tumor sites and effectively delivered their cargo (e.g., oncolytic viruses or nanoparticles) to the tumors. As described herein, adoptively transferred MDSCs labeled with the nanoparticle ferumoxides preferentially migrated into tumors with label intact, demonstrating both that MDSCs were able to reach the tumor with limited phagocytosis and metabolism of the ferumoxides label, and that MDSCs are effective carriers of exogenous substances (e.g., anti-tumor agents, such as nanoparticles) to tumor sites. MDSCs were also demonstrated herein to delivery aluminum peroxide based nanoparticles conjugated to tumor antigen or TLR ligand to tumor sites and to deliver them with much greater efficiency compared to system delivery of the nanoparticles.

Survival rates in tumor-bearing mice treated with MDSCs in combination with VSV were significantly improved when compared to mice treated with other types of cells in combination with VSV, or compared to mice treated with similar doses of intravenous VSV alone. Similarly, tumor-bearing mice treated with MDSCs loaded with aluminum peroxide nanoparticles conjugated to tumor antigen or the TLR ligand PGN had significantly increased survival rates, indicating that MDSCs loaded with nanoparticles can be used therapeutically to treat tumors and metastases.

MDSCs suppress the host immune response, in part through the induction of regulatory T cells. Without being bound by theory, the use of MDSCs for the delivery of oncolytic viruses and/or other anti-tumor agents advantageously provides prolonged therapy, compared to known methods, by delaying or preventing the onset of host rejection of the MDSCs and/or anti-tumor agents (e.g., oncolytic viruses) used to specifically treat tumors.

In certain embodiments, the present invention is also based in part on the discovery that MDSCs responsible for tumor killing have an M1 phenotype with viral infection and/or with TLR ligand delivery with nanoparticles (NP).

Methods for diagnosing tumors in a subject are provided. In one embodiment, the method for diagnosing a tumor comprises: (i) administering to the subject labeled myeloid derived suppressor cells (MDSCs); and (ii) determining whether said labeled MDSCs become concentrated in at least one site in said subject. In a specific embodiment, the method for diagnosing a tumor in a subject further comprises performing a PET scan on said subject to confirm the diagnosis of the tumor.

In certain embodiments, compositions comprising MDSCs and anti-tumor agents, such as oncolytic viruses or nanoparticles, are provided and are useful for treating tumors in a patient. In certain embodiments, compositions and methods for treating tumors provide significantly improved therapeutic efficacy of oncolytic viruses for the treatment of tumors by providing a novel method for their targeted delivery to tumors using MDSCs. Such methods and compositions overcome the current lack of effective carriers for delivery to tumor sites, a major hindrance of oncolytic viral delivery. In a specific embodiment, a composition comprises MDSCs and vesicular stomatitis virus (VSV) or the adenovirus AdlTRAIL-EI.

In certain embodiments, compositions comprise MDSCs and other anti-tumor agents, such as chemotherapeutic drugs or other small molecules. Such compositions are useful for delivery of the chemotherapeutic drugs or other small molecules to tumors.

In certain embodiments, a composition comprises an MDSC and a nanoparticle. In some embodiments, the nanoparticle is conjugated to another anti-tumor agent, as provided herein. For example, a nanoparticle may be conjugated to one or more adjuvants and/or to one or more antigens. In a specific embodiment, an antigen is a tumor antigen. In another specific embodiment, an adjuvant is a Toll-like receptor ligand (TLRL) adjuvant, such as peptidoglycan (PGN) or LPS or CpG. Preferably, although not necessarily, the MDSC has taken up (e.g., phagocytosed) the nanoparticle. In other embodiments, a nanoparticle may be conjugated to one or more chemotherapeutic agents and/or one or more antigens and/or adjuvants.

DEFINITIONS

The term "myeloid derived suppressor cell (MDSC)" refers to a cell with an immunosuppressive function that is of hematopoietic lineage.

The terms "MDSC and an anti-tumor agent" and "MDSC in combination with an anti-tumor agent" mean that the MDSC is coupled to and/or associated with the anti-tumor agent such that both the MDSC and the anti-tumor agent reach the intended target (tumor site), or such that at least the anti-tumor agent is delivered by the MDSC to the tumor site. In certain embodiments, the terms "MDSCs in combination with an oncolytic virus" and "MDSCs and an oncolytic virus" mean that the MDSC is coupled to and/or associated with the virus such that both the MDSC and the virus reach the intended target (tumor site), or that at least the virus is delivered by the MDSC to the tumor site. The MDSCs can be infected with the virus or conjugated to the virus (e.g., using an antibody or other suitable conjugation method). In a specific embodiment, an MDSC is conjugated to VSV using a monoclonal antibody specific for the G protein on the surface of VSV. The MDSC binds to the Fc portion of the antibody bound to VSV, thereby conjugating the MDSC to the VSV particle; this conjugate is therefore a specific example of an "MDSCs in combination with an oncolytic virus." It is not required, though it is possible, for the MDSCs to be actively infected with the oncolytic virus.

As used herein, the term "tumor" refers to a malignant tissue comprising transformed cells that grow uncontrollably. As used herein, the term "tumor" encompasses cancer. The term "cancer" refers to all types of cancer, neoplasm or malignant tumors found in mammals, including without limitation leukemia, carcinomas and sarcomas.

The term "anti-tumor agent" refers to any agent, which has a therapeutic effect for the treatment of a tumor (including cancer). Non-limiting examples of anti-tumor agents include oncolytic viruses, (e.g., VSV, adenoviruses), chemotherapeutic drugs (e.g., taxoids), or other small molecules that target tumor cells. The term "target a tumor cell" with respect to an anti-tumor agent means that the anti-tumor agent inhibits tumor growth. The terms "treating a tumor" and "inhibits/inhibiting tumor growth" are used interchangeably and refer to a decrease in the rate of tumor growth, and/or in the size of the tumor and/or in the rate of local or distant tumor metastasis in the presence of a composition of the invention, and/or any decrease in tumor survival, and can include treating cancer.

As used herein, the terms "chemotherapeutic agent" and "chemotherapeutic drug" are used interchangeably and refer to a compound that is capable of inhibiting, disrupting, preventing or interfering with cell growth and/or proliferation. Examples of chemotherapeutic agents include, but are not limited to, agents which induce apoptosis, necrosis, mitotic cell death, alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, steroid hormones and anti-androgens.

Chemical agents, referred to in the art as "small molecule" compounds are typically organic, non-peptide molecules, having a molecular weight less than 10,000 Da, preferably less than 5,000 Da, more preferably less than 1,000 Da, and most preferably less than 500 Da. This class of modulators includes chemically synthesized molecules, for instance, compounds from combinatorial chemical libraries. Synthetic compounds may be rationally designed or identified utilizing screening methods. Alternative appropriate modulators of this class are natural products, particularly secondary metabolites from organisms such as plants or fungi, which can also be identified by screening compound libraries for tumor-killing activity. Methods for generating and obtaining small molecules are well known in the art (Schreiber, *Science* 2000; 151:1964-1969; Radmann et al., *Science* 2000; 151: 1947-1948).

The term "subject," "patient" or "individual" as used herein refers to an animal having an immune system, preferably a mammal (e.g., rodent, such as mouse). In particular, the term refers to humans. As used herein, the term "mammal" has its ordinary meaning, and specifically includes primates, and more specifically includes humans. Other mammals that may be treated for the presence of a tumor, or in which tumor cell growth may be inhibited, include, but are not limited to, canine, feline, rodent (racine, murine, lupine, etc.), equine, bovine, ovine, caprine, and porcine species.

As used herein, the term "isolated" means that the material being referred to has been removed from the environment in which it is naturally found, and is characterized to a sufficient degree to establish that it is present in a particular sample. An isolated organelle, cell, or tissue is one that has been removed from the anatomical site (cell, tissue or organism) in which it is found in the source organism. An isolated material may or may not be "purified," as defined herein. The term "purified" as used herein refers to a material (e.g., a cell) that has been isolated under conditions that detectably reduce or eliminate the presence of other contaminating materials. Contaminants may or may not include native materials from which the purified material has been obtained. A purified material preferably contains less than about 90%, less than about 75%, less than about 50%, less than about 25%, less than about 10%, less than about 5%, or less than about 2% by weight of other components with which it was originally associated.

"Treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving the disease, i.e., causing regression of the state, disorder or condition or at least one of its clinical or subclinical symptoms.

As used herein "combination therapy" or "adjunct therapy" means that a patient in need of treatment with a certain composition or drug is treated or given another composition or drug for the disease in conjunction with the first composition or drug. Combination therapy can be sequential therapy where the patient is treated first with one composition or drug and then the other, or alternatively, the two drugs can be given simultaneously. In either case, these drugs are said to be "co-administered." For example, an MDSC of the invention may be administered in a combination therapy for the treatment of a tumor or metastasis along with another anti-tumor therapy. For example, the MDSC may be administered in a combination therapy with sunitinib malate. Sunitinib malate is an oral multitargeted tyrosine kinase inhibitor with antitumor and antiangiogenic activity that recently received approval from the FDA for the treatment of advanced renal cell carcinoma and of gastrointestinal stromal tumours after disease progression on or intolerance to imatinib mesilate therapy. Sunitinib has also demonstrated promising clinical activity in the treatment of other advanced solid tumours. See, Motzer et al. (2006) *Expert Opin Investig Drugs;* 15(5):553-61.

The term "pharmaceutically acceptable derivative" as used herein means any pharmaceutically acceptable salt, solvate or prodrug, e.g., ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

As used herein the terms "therapeutically effective" and "effective amount", used interchangeably, applied to a dose or amount refers to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using enhanced tumor growth inhibition and/or enhanced cancer survival rates as a readout.

Compositions

In certain aspects, compositions comprising an isolated MDSC and an anti-tumor agent, such as an oncolytic virus, chemotherapeutic agent or other small molecule are provided. In a specific embodiment, a composition comprises an isolated MDSC and VSV or the adenovirus AdlTRAIL-EI. In certain embodiments, a composition comprises an MDSC and a nanoparticle. In certain embodiments, the nanoparticle is conjugated to an adjuvant and/or to an antigen. In a specific embodiment, the antigen is a tumor antigen. In another specific embodiment, the adjuvant is a Toll-like receptor ligand (TLRL) adjuvant, such as peptidoglycan (PGN) or CpG or LPS. Preferably, the MDSC has taken up (e.g., phagocytosed) the nanoparticle.

In another embodiment, a nanoparticle may be conjugated to multiple agents, such as, e.g., multiple antigens and/or adjuvants. In a specific embodiment, a nanoparticle is conjugated to at least two different TLR ligands, such as, a TLR2 ligand and a TLR9 ligand, or a TLR2 ligand and a TLR4 ligand. The skilled artisan will appreciate that other combinations of TLR ligands are also possible. In other embodiments, MDSCs may be loaded with one or more TLR ligands or antigens directly, without nanoparticles.

Myeloid Derived Suppressor Cells (MDSCs)

Murine MDSCs, which are also known as myeloid suppressor cells (MSCs), can be identified by the expression of one or more of the cell surface markers CD11b, Gr1, CD115, Ly6C, and F4/80 [see, Li et al., Cancer Res. 2004, 64:1130-1139]. Murine MDSCs, typically express, for example, CD11b, CD115, Gr1 and Ly6C. Murine MDSCs may also express CD31, c-kit, vascular endothelial growth factor (VEGF)-receptor, and/or CD40.

Human MDSCs can be identified by expression of one or more of the cell surface markers CD11b, CD33, CD34, CD14, CD15 and/or CD16, depending on the particular subset. Human MDSCs typically express, for example, CD11b and CD33 alone or in combination with one or more of CD34, CD14, CD15 and/or CD16 and/or other cell surface markers. Non-limiting examples of 4 subsets of human MDSCs include CD11b+CD33+CD14+ MDSCs, CD11b+CD33+CD14+CD16+ MDSCs, CD11b+CD33+CD115+HLA-DRlowIL-4R+ MDSCs, and CD11b+CD33+CD15+ MDSCs. Murine and human MDSCs and the cell surface markers expressed on these cells are described in detail in International Patent Application No. PCT/US09/65981 by Chen et al.

MDSCs can be induced to differentiate into mature granulocytes, macrophages, and dendritic cells upon culture in the presence of the appropriate cytokine cocktail [Apolloni et al., 2000, J. Immunol. 165:6723-6730; Bronte et al., 2000 Blood 96: 3838-46; Kusmartsev et al., 2003, Cancer Res. 63:4441-4449; Li et al., 2004, Cancer Res. 64:1130-1139]. MDSCs can also spontaneously differentiate in culture and express lineage markers such as CD11c, MHC molecules (class I and class II), F4/80, costimulatory molecules (e.g., CD80 and CD86), M1 or M2 macrophage. It is presently discovered that tumor-trophic MDSCs can be converted from the M2 (pro-tumor and pro-angiogenic) to M1 (antitumor) phenotype and subsequently used as tumor-targeting vehicles to carry therapeutic viruses, thereby inhibiting the growth of primary and metastatic tumors. The M1 functional phenotype include high iNOS, TNFα, CCR7, IL-6, expression vs. M2 functional phenotype, e.g. CD206, Arginase I (Arg), CD36, IL-10, IL-4 Receptor (IL-4R), Tie2 expression. See, Umemura N et al. (2008) *J Leukoc Biol;* 83:1136-44; Ma et al. (2011) Paired immunoglobin-like receptor-B regulates the suppressive function and fate of myeloid-derived suppressor cells. Immunity; 34:385-95.

The isolation of or in vitro generation of MDSCs for use in the present compositions is described in detail in International Patent Application Publication No. WO 2010/062990 by Chen. An "isolated MDSC" includes an MDSC obtainable by any suitable method that is or has been removed from its natural environment (if MDSC is isolated from a living source), or that is derived in vitro. An isolated MDSC that has been removed from its natural environment may be returned to that environment or another site subsequent to isolation.

In some embodiments of the invention, MDSCs are autologously-derived cells. For example, MDSCs can be isolated from normal adult bone marrow or from sites of normal hematopoiesis, such as the spleen. MDSCs are scant in the periphery and are present in a low number in the bone marrow of healthy individuals. However, they are accumulated in the periphery when intense hematopoiesis occurs. Upon distress due to graft-versus-host disease (GVHD), cyclophosphamide injection, or γ-irradiation, for example, MDSCs can be found in the adult spleen. Thus, in certain embodiments, MDSCs can be isolated from the adult spleen. MDSCs can also be isolated from the bone marrow and spleens of tumor-bearing or newborn mice.

In certain embodiments, MDSCs are isolated in vivo by mobilizing MDSCs from hematopoietic stem cells (HSCs) or bone marrow using stem cell mobilizers such as G-CSF (R&D Systems®, Minneapolis, Minn.), GM-CSF (R&D Systems, Minneapolis, Minn.), AMD 3100 (Tocris Bioscience, Ellisville, Mo.) [see, Larochelle, A. et al. (2006) Blood, Vol. 107 (9):3772-3778], CTCE-9908 (Chemokine Therapeutics Corp.), FTY720 (Cayman Chemical, Ann Arbor, Mich.) [see, Kimura, T. et al. (2004) Blood; June 15; 103(12):4478-86], M-CSF and/or Flt3 ligand (R&D Systems®). Any suitable stem cell mobilizer or combination of mobilizers is contemplated for use in the present invention. MDSCs may then be collected from the blood e.g., by apheresis, cell sorting and magnetic purification procedure.

In certain embodiments, MDSCs can be derived, for example, in vitro from a patient's hematopoietic stem cells (HSCs), from MHC matching embryonic stem (ES) cells, and/or from induced pluripotent stem (iPS) cells [see, Baker, Monya (2007). "Adult cells reprogrammed to pluripotency, without tumors". *Nature Reports Stem Cells*. published online]. Methods for expanding MDSCs in vitro are described in detail in U.S. Publication No. 2008/0305079 by Chen. Specifically, isolated HSCs can be stimulated to differentiate into Gr-1+/CD11b+, Gr-1+/CD11b+/CD115+, Gr-1+/CD11b+/F4/80+, or Gr-1+/CD11b+/CD115+/F4/80+ MDSCs by culturing the HSCs in the presence of stem-cell factor (SCF) or SCF with tumor factors, which can increase the MDSC population. The culture conditions for mouse and human HSCs for differentiating HSCs into MDSCs are described in detail in U.S. Publication No. 2008/0305079 by Chen.

In further embodiments, other cytokines may be used, e.g., GM-CSF, M-CSF, or G-CSF (all commercially available, e.g., from R&D Systems®) to stimulate MDSC differentiation from HSCs in vitro. Any one of the cytokines may be used alone or and SCF or other cytokines. In still another embodiment, tumor-conditioned media may be used with or without SCF to stimulate HSCs to differentiate into MDSCs.

In other embodiments, MDSCs are allogeneic cells, such as MDSCs obtained or isolated from a donor or cell line. MDSC cell lines and exemplary methods for their generation are well known in the art and are described in the literature. [See, e.g., Apolloni et al. (2000) "Immortalized myeloid suppressor cells trigger apoptosis in antigen-activated T lymphocytes." *J. Immunol.* 165:6723; Mazzoni et al. (2002) "Myeloid Suppressor Lines Inhibit T Cell Responses by an NO-Dependent Mechanism;" *J. Immunol.* 168:689-695.]

MDSCs obtainable by any method or from any suitable source are contemplated for use in the compositions and methods provided herein.

Oncolytic Viruses

Any suitable oncolytic virus is contemplated for use in the present compositions. For example, vesicular stomatitis virus (VSV) is a rhabdovirus with oncolytic properties that will infect a wide variety of mammalian cells. VSV preferentially replicates in, and lyses tumor cells due to their ability to avoid host interferon responses, which interfere with viral reproduction enabling host immune clearance [see, Thomsen A R, et al. Cooperation of B cells and T cells is required for survival of mice infected with vesicular stomatitis virus. Int Immunol. 1997; 9(11):1757-66]. VSV has been shown effective at prolonging the survival of mice when injected intratumorally in the metastatic MCA26 tumor model [see, Huang T G, et al. Oncolysis of hepatic metastasis of colorectal cancer by recombinant vesicular stomatitis virus in immune-competent mice. Mol. Ther. 2003; 8(3):434-40]. Virus may thus be administered by intratumoral administration. Virus may also be administered by peripheral administration. Peripheral administration decreases the risks associated with surgery (e.g., for intratumoral administration). Simply injecting free virus intravenously typically leads to only a small fraction of virus reaching the tumor site, necessitating large doses of virus to be injected peripherally to achieve similar doses as can be obtained via intratumoral administration. VSV mutant, rVSV(MΔ51)-M3 mutant, has been engineered to express the gammaherpesvirus protein M3 on its surface, leading to significantly decreased antiviral clearance by the host immune system. The M3 virus elicits a potent oncolytic response in tumors [see, Wu L, et al. rVSV(M Delta 51)-M3 is an effective and safe oncolytic virus for cancer therapy. Hum Gene Ther. 2008; 19(6):635-47]. VSV mutants, such as M3 virus and others, are also contemplated for use in the present compositions and methods. It is to be understood, however, that the compositions and methods described herein are not limited to VSV and VSV mutants. Other oncolytic viruses may also be used in combination with MDSCs, as described herein.

Adenoviruses are a class of oncolytic viruses. To date, roughly 50 different serotypes of human adenovirus have been discovered. Adenoviruses possess linear, double-stranded, non-enveloped DNA genomes. The adenovirus life-cycle involves integrin binding with the cocksackie and adenovirus receptor (CAR) with subsequent viral entry into the tumor cell. Once intracellular, the virus migrates further into the nucleus, begins expression of early-region gene products and prevents activation of multiple apoptosis mechanisms. At this point, the viruses block the synthesis of host cell proteins and, instead, begin self-DNA replication and protein synthesis. The E3 region of the viral genome encodes multiple proteins that aid in evading host immune responses (Wold et al, 1995; Dimitrov et al., 1997). Specifically, the gp19kD protein prevents MHC-class I expression on the cell surface, which helps avoid cytotoxic T-lymphocyte mediated killing) and the E3 10.4/14.5 kD and 14.7 kD proteins downregulate FasL- or TNF-mediated apoptosis pathways (Dimitrov et al., 1997, Shisler et al, 1996). Adenoviruses include, e.g., AdI-TRAIL-EI; the P53 oncolytic virus ONYX-015, which is an E1B-55 kDa gene-deleted adenovirus engineered to selectively replicate in and lyse p53-deficient cancer cells that can be used to target head and neck cancer [see, Kutler, D. et al. Molecular Therapy; (2006) 13, S168], CV706, a prostate-specific adenovirus, OncoVEX$^{GM-CSF}$ (BioVex), JX-584 (Jennerex), CGTG-102 (Oncos Therapeutics), reovirus and poliovirus.

Oncolytic viruses can be directly conjugated to MDSCs in order to increases the efficiency of coupling and to increase the number of viral particles conjugated to each cell. In certain embodiments, a non-neutralizing monoclonal antibody directed against the G protein on the surface of VSV was utilized. Upon binding the virus, the antibody is then bound to Fc receptors present on the surface of MDSCs, thus increasing the binding efficacy between virus and cell. Antibodies specific for viral surface antigens are known in the art, and may be used to couple other oncolytic viruses to MDSCs, as described herein for VSV.

Anti-Tumor Agents

For the treatment of tumors, including for the treatment of cancers and other hyperproliferative disorders, anti-tumor agents (e.g., tumor growth inhibitors), in addition to the oncolytic viruses disclosed above, include but are not limited to chemotherapeutic agents, for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phospatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815.

In other embodiments, anti-tumor agents include but are not limited to interferon (IFN)-gamma, tumor necrosis factor (TNF)-alpha, TNF-beta, and similar cytokines. Alternatively, an anti-tumor agent can be an antagonist of a tumor growth factor. Such antagonists include, but are not limited to, antagonists of tumor growth factor (TGF)-beta and IL-10.

Anti-tumor agents can be conjugated to MDSCs, by any suitable method. By way of a non-limiting example, such agents can be conjugated using an antibody that binds to MDSCs. Such MDSC-anti-tumor agent-conjugating antibodies can bind to any cell surface marker expressed on MDSC, e.g., anti-Gr-1, anti-CD116, or anti-Ly6C. The MDSC-anti-tumor agent conjugating antibody can also bind to Fc receptors expressed on MDSCs. As a specific example, MDSCs can be conjugated via the Fc receptor to the Her 2-neu antibody conjugated with DM-1 (which is a chemotherapeutic agent that targets microtubules) [see, e.g. http://news.oneindia.in/2010/10/09/newtherapy-shows-promising-result-for-her2-positivemetasta.html]. The Her-2 neu antibody can also be conjugated to another or different anti-tumor agent, for example, one which inhibits tumor cells from dividing.

In other embodiments, the anti-tumor agent can be an anti-angiogenic factor, which is a molecule that inhibits angiogenesis, particularly by blocking endothelial cell migration. Such factors include fragments of angiogenic proteins that are inhibitory (such as the ATF of urokinase), angiogenesis inhibitory factors, such as angiostatin and endostatin; soluble receptors of angiogenic factors, such as the urokinase receptor or FGF/VEGF receptor; molecules which block endothelial cell growth factor receptors (O'Reilly et. al. Cell 1997, 88:277-285; and O'Reilly, Nat. Med. 1996, 2:689-692), and Tie-1 or Tie-2 inhibitors. Generally, an anti-angiogenic factor for use in the invention is a protein or polypeptide. Examples of anti-angiogenic factors include, but are not limited to, the amino terminal fragment (ATF) of urokinase, containing the EGF-like domain (e.g., amino acid residues about 1 to about 135 of ATF); ATF provided as a fusion protein, e.g., with immunoglobulin or human serum albumin (PCT Publication No. WO 93/15199); angiostatin (O'Reilly et al., Cell 1994, 79:315-328); tissue inhibition of metalloproteinase (Johnson et al., J. Cell. Physiol. 1994, 160:194-202); or inhibitors of FGF or VEGF such as soluble forms of receptors for angiogenic factors, including but not limited to soluble VGF/VEGF receptor, and soluble urokinase receptor (Wilhem et al., FEBS Letters 1994, 337:131-134). The present invention contemplates administration of anti-angiogenesis factors systemically, or alternatively by gene therapy or any other suitable method.

It is shown in the present Examples that MDSCs efficiently phagocytose ferumoxides nanoparticles and deliver oncolytic viruses specifically to tumor sites. It is also demonstrated in the present Examples that MDSCs deliver other aluminum peroxide-based nanoparticles conjugated to protein antigens and TLR ligands (e.g. OVA, tumor antigens, and PGN) to tumors and sites of metastasis. Such aluminum peroxide-based nanoparticles are described in detail in Li et al. (2011) Nat. Nanotechnol.; 6(10):645-50. Currently there are multiple groups working on loading a variety of treatments into nanoparticles, from chemotherapeutic agents [see, Kang K W, et al. Doxorubicin loaded solid lipid nanoparticles to overcome multidrug resistance in cancer therapy. Nanomedicine. 2010 April; 6(2):210-3] to siRNA [see, Li L, et al. Evaluation of specific delivery of chimeric phi29 pRNA/siRNA nanoparticles to multiple tumor cells. Mol. Biosyst. 2009; 5(11): 1361-8]; these agents and small molecules and combinations thereof can be loaded into MDSCs according to the presently described methods. By targeting treatments specifically to the tumor, it is possible to achieve higher intratumoral concentrations of these therapeutic agents, while keeping the systemic doses low. Thus, in a preferred embodiment, the invention provides a method for treating a tumor and/or a metastasis by administering to a subject an MDSC comprising a nanoparticle. The nanoparticle can be conjugated to any desired agent for treating the tumor or metastasis, such as a tumor antigen useful for eliciting an anti-tumor immune response, a TLRL adjuvant or other adjuvant known in the art, or a chemotherapeutic agent. In certain embodiments, a composition comprises an MDSC and a nanoparticle. In certain embodiments, the nanoparticle is conjugated to an adjuvant and/or to an antigen. In a specific embodiment, the antigen is a tumor antigen. In another specific embodiment, the adjuvant is a Toll-like receptor ligand (TLRL) adjuvant, such as peptidoglycan (PGN) or LPS or CpG. In another embodiment, the nanoparticle is conjugated to multiple agents, such as, e.g., multiple TLR ligands. In a preferred embodiment, the nanoparticle comprises, e.g., is conjugated to PGN and CpG. Such nanoparticle may also be conjugated to or associated with additional agents, e.g., peptide antigens, such as tumor antigens.

It is to be understood that the nanoparticle described herein are meant to be non-limiting examples of nanoparticles. The present invention contemplates the use of any nanoparticle suitable for the delivery of a desired agent or agents to a tumor cell, such as, but not limited to anti-tumor agent(s) (chemotherapeutic agent(s), adjuvant(s) (e.g., TLR ligand(s)), tumor antigen(s), etc.). Preferably, the nanoparticle is delivered to a tumor site and/or metastasis by an MDSC according to the present invention.

TLRL adjuvants and agonists are well known in the art. Non-limiting examples contemplated for use herein include all TLR agonists (pathogen-associated molecular patterns, PAMP, activator): such as, but not limited to, lipopolysaccharide (LPS), peptidoglycan (PGN), and CpG, PolyIC, the TLR4 agonist–monophosphoryl Lipid A, recombinant flagellin, ssRNA with 6 UUAU (SEQ ID NO: 5) repeats/LyoVec, and others.

Formulations

Compositions can be formulated for administration in any convenient way for use in human or veterinary medicine. The MDSCs can be incorporated into liposomes, microemulsions, micelles, unilamellar or multilamellar vesicles, erythrocyte ghosts or spheroblasts. In one embodiment, the MDSCs can be delivered in one or more vesicles, including as a liposome (see Langer, Science, 1990; 249:1527-1533; Treat et al., in Liposomes in the Therapy of Infectious Disease and Cancer, Lopez-Berestein and Fidler (eds.), Liss: New York, pp. 353-365 (1989); Lopez-Berestein, ibid., pp. 317-327; see generally ibid.).

MDSCs can also be delivered in a controlled release form. For example, MDSCs may be administered in a polymer matrix such as poly (lactide-co-glycolide) (PLGA), in a microsphere or liposome implanted subcutaneously, or by another mode of delivery (see, Cao et al., 1999, Biomaterials, February; 20(4):329-39). Another aspect of delivery includes the suspension of the compositions in an alginate hydrogel.

MDSCS and anti-tumor agents can be formulated as an injectable or inhalable solution, such as a solution containing PBS, with or without other ingredients.

The present invention also provides pharmaceutical formulations or dosage forms for administration to mammals in need thereof.

The subject invention also concerns the use of MDSCs in the preparation of a pharmaceutical formulation. Pharmaceutical formulations may include, for example, MDSCs and one or more anti-tumor agents, such as those described above (e.g., oncolytic viruses and/or chemotherapeutic agents).

While it is possible to use a composition for therapy as is, it may be preferable to administer compositions as pharmaceutical formulations, e.g., in admixture with a suitable pharmaceutical excipient, diluent, or carrier selected with regard to the intended route of administration and standard pharmaceutical practice. Pharmaceutical formulations comprise at least one active compound, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Pharmaceutical formulations may comprise, for example, and without limitation, an isolated MDSC and an anti-tumor agent and a pharmaceutical carrier. Pharmaceutical formulations may also comprise, e.g., an isolated MDSC and an oncolytic virus, such as but not limited to VSV, AdlTRAIL-EI and/or rVSV(MΔ51)-M3, and a pharmaceutical carrier. In a preferred embodiment, a pharmaceutical formulation comprises an isolated MDSC and a chemotherapeutic agent, and a pharmaceutical carrier. In certain aspects, an MDSC and anti-tumor agent are each administered separately to a patient in need of treatment as separate pharmaceutical formulations. Pharmaceutical formulations may be administered separately or together, at the same or different sites, at the same or different times.

Tumor Diagnosis

In certain embodiments, a method for diagnosing a tumor in a subject is provided. This method takes advantage of the present discovery that adoptively transferred MDSCs migrate preferentially to tumors. Tumors may be diagnosed by, e.g., administering a labeled MDSC to a subject and detecting the MDSC label in vivo, to determine the presence and location of a tumor. MDSCs are labeled with a marker that can be tracked in vivo, such as, for example a radioisotope, or other suitable labels which may be visualized according to known medical techniques, e.g., magnetic resonance imaging (MRI) or X-ray. In a specific embodiment, the label is ferumoxides (e.g., Ferridex®, Berlex; Montville, N.J.), which is a detectable label that is approved by the FDA for human use. Other labeling methods include using, e.g., Indium (In 111) label, which has been used clinically and in pet scans. Antibody-labeled isotopes, e.g., Iodine 131 or 125 can be used. Such antibody-isotope conjugates can bind to MDSCs to track MDSC migration and to locate micrometastases. Any suitable labeling method can be used to track MDSCs in vivo.

Such methods may be used, therefore, to diagnose a tumor, micrometastasis or metastasis, wherein a high concentration of labeled MDSCs at a site are diagnostic of the presence of a tumor. Diagnosis methods may also be combined with treatment, e.g., by administering a labeled MDSC and an anti-tumor agent, wherein the diagnosis steps are carried out, while simultaneously, the anti-tumor agent treats the tumor.

Methods of Treatment

The present invention provides for use of compositions comprising MDSCs and anti-tumor agents for targeting anti-tumor agents to tumor cells, e.g., for the treatment of tumors (e.g., inhibiting tumor growth).

Tumors include without limitation leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Further, as discussed above, the term tumor encompasses cancer. Exemplary cancers include without limitation cancer of the breast, brain, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

The MDSC-containing compositions may be used to treat a tumor by, e.g., targeting oncolytic viruses or chemotherapeutic agents to a tumor. A composition or pharmaceutical formulation comprising MDSCs and an oncolytic virus is typically, without limitation, administered to a patient in need of treatment (i.e., a patient with a tumor or cancer). Thus, a composition or pharmaceutical formulation comprising MDSCs and a chemotherapeutic agent may be administered to a patient in need of such treatment. In certain embodiments, the anti-tumor agent is a small molecule that inhibits tumor growth.

A patient administered an MDSC-containing composition can be co-treated in a combination therapy, for example, with other anti-tumor treatment modalities, such as, e.g., radiation therapy and/or surgery and/or chemotherapy, such as any of those described above, or with another treatment modality.

For example, as described above, the MDSC may be administered in a combination therapy with sunitinib malate. Sunitinib malate is an oral multitargeted tyrosine kinase inhibitor with antitumour and antiangiogenic activity that recently received approval from the FDA for the treatment of advanced renal cell carcinoma and of gastrointestinal stromal tumours after disease progression on or intolerance to imatinib mesilate therapy. Sunitinib has also demonstrated promising clinical activity in the treatment of other advanced solid tumours. See, Motzer et al. (2006) Expert Opin Investig Drugs; 15(5):553-61. It is demonstrated in the present Examples, below, that tumor-bearing mice treated with an MDSC of the invention (e.g., an MDSC that had loaded with antigen or TLR ligand bearing nanoparticle or loaded with an oncolytic virus) can be advantageously administered with sunitinib malate to achieve an even more improved therapeutic benefit to the host. Of course, it is to be understood that the present Examples also demonstrate that MDSCs of the invention have excellent therapeutic benefits for the treatment of tumors and/or metastases even without sunitinib malate co-administration. While not intending to be bound by theory or a particular mechanism of action, MDSCs can be used for the treatment of tumors and metastases, for example, because they are discovered herein to be highly tumor trophic cells that successfully deliver anti-tumor agents directly to a target tumor and/or a metastatic site. They also may suppress host rejection of oncolytic viruses, as described herein.

Co-administration of an MDSC-containing composition and another treatment modality may be at the same or different sites, at the same or at different times, and/or for the same or different durations, amounts and frequencies. The skilled artisan will understand when it would be appropriate or desirable to use a combination therapy, such as sunitinib malate, depending on the patient and the tumor type.

Administration

Compositions and formulations can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). The preferred route of MDSC administration is intravenous (i.v.). However, MDSCs can also be administered intraperitoneally, subcutaneously or mucosally (e.g, by oral or nasal administration). The preferred route of administration for anti-tumor agents, when administered separately from MDSCs is intravenous (i.v.). The MDSCs and anti-tumor agents of the invention may be administered in any way known in the art.

Compositions may be administered once a day, twice a day, or more often. Frequency may be decreased during a treatment maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

It will be appreciated that the amount of MDSCs and/or anti-tumor agents required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Exemplary dosages of MDSCs for administration to humans range from about $5\times10^6$ to about $5\times10^8$ or higher, although lower or higher numbers of MDSCs are also possible. Methods in which autologous MDSCs are administered are advantageous, in that there is little to no toxicity. In a preferred embodiment, a patient can receive, for example, $5\times10^7$-$5\times10^{10}$ MDSCs.

Length of treatment, i.e., number of days, will be readily determined by a physician treating the patient, however the number of days of treatment may range from 1 day to about 20 days. MDSCs are preferably administered at a frequency of about once every 7 days to about once every day. More preferably, MDSCs are administered at a frequency of about once or twice every day.

Kits

In certain embodiments, a kit for treating a tumor in a subject or patient is provided. The kit comprises isolated MDSCs and at least one anti-tumor agent. The MDSCs and anti-tumor agent(s) may be contained together in the kit (e.g. pre-conjugated or, in a specific embodiment, the MDSCs can be pre-infected with an oncolytic virus, or each component can be provided separately, to be combined prior to or at the time of use (administration to the subject or patient). Optionally, the kit provides instructions for use.

Kits may include material for diagnosing a tumor in a subject or patient. Such kits comprise, e.g., an isolated MDSC labeled with a marker that is detectable in vivo. In a specific embodiment, the marker is ferumoxides, although other markers are also contemplated. Kits may also include instructions for use.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.; Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The present invention is further described by way of the following examples. The use of such examples is illustrative only and is not intended to limit the scope or meaning of this invention or of any exemplified term. Nor is the invention limited to any particular preferred embodiment(s) described herein. Indeed, many modifications and variations of the invention will be apparent to those skilled in the art upon reading this specification, and such "equivalents" can be made without departing from the invention in spirit or scope. The invention is therefore limited only by the terms of the appended claims, along with the full scope of equivalents to which the claims are entitled.

EXAMPLES

In the examples below, the following materials and methods were used.

Experimental Animals

Wild type (WT) BALB/c mice were purchased from Jackson Laboratories (Bar Harbor, Me.). All animal experiments were performed in accordance with the guidelines of Mount Sinai School of Medicine.

Congenic CD45.1+ C57BL/6, ovalbumin (OVA)-specific MHC class II-restricted TCR-transgenic (OT-II) C57BL/6, CCR2 knockout (KO) C57BL6, MHC class I KO C57BL/6, MHC class II KO C57BL/6, were purchased from National Cancer Institute and The Jackson Laboratory. CCR7 knockout (KO) C57BL/6 mice were a gift from Dr. Gwen Randolph (Mount Sinai School of Medicine).

Antibodies and Flow Cytometry

Anti-Ly6C-FITC, anti-Ly6C-PE, anti-CD11b-APC, anti-Gr-1-PE-Cy5, and isotype-matched mAbs were purchased from eBioscience (San Diego, Calif.). PKH26 fluorescent membrane linker dye was purchased from Sigma Aldrich (St. Louis, Mo.). Flow cytometric analyses were performed using FACSCanto II and FACSDiVa software (BD Biosciences; San Jose, Calif.).

Mouse anti-CD4 fluorescein isothyocyanate (FITC), mouse anti-CD25 PE-Cy7, mouse anti-CD115 phycoerythrin (PE), mouse anti-F4/80 allophycocyanin (APC), mouse anti-Foxp3 PE, mouse anti-CD36 APC, mouse anti-CD11c PerCP-Cy5.5, mouse anti-Thy1.2-FITC, and isotype-matched mAbs were purchased from eBioscience (San Diego, Calif.), and anti-CD206-biotin was purchased from AbDSerotec (Raleigh, N.C.). Anti-Mouse Siglec-1/CD169 Biotin was purchased from R&D Systems (Minneapolis, Minn.). Anti-iNOS (inducible nitric oxide synthase) FITC was purchased from BD Pharmingen, Anti-Arginase 1 (San Diego, Calif.), and isotype-matched monoclonal anti-bodies were purchased from eBioscience (San Diego, Calif.).

PKH26 Cell Migration

For PKH26 analysis, MDSCs were stained with PKH26 via manufacturer specifications and adoptively transferred via tail vein into BALB/c mice bearing intrahepatic MCA26 colon cancer 14 days after inoculation. Representative mice were sacrificed daily and spleen, bone marrow, lymph nodes, liver, lung, and tumor were harvested. Organs were homogenized and immune cells were isolated, stained for MDSC markers, and analyzed via FACS. Murine organs were also fixed with O.C.T. compound (Tissue-Tek; Torrence, Calif.), sectioned, and stained with Perl's Prussian blue to indicate the presence of iron.

Isolation of Monocytic MDSCs

WT BALB/c or C57Bl/6 mice were injected subcutaneously with $5 \times 10^5$ MCA26 murine colon cancer cells or $5 \times 10^5$ Lewis Lung Cancer (LLC) cells (respectively). Mice were sacrificed when tumors reached 1×1 cm in size and splenocytes and bone marrow were processed to single cell suspensions. Red blood cells were lysed with ACK lysing buffer (Gibco; Carlsbad, Calif.). Monocytic cells were then isolated from fraction 2 of a percoll density gradient (GE Healthcare, UK). Cells were stained in the presence of FcγR blocking Ab with Ly6C-FITC and bound to anti-FITC microbeads (Miltenyi; Auburn, Calif.). Ly6C+ and Ly6C− cells were sorted via AutoMACS cell sorter (Miltenyi) and counted via trypan blue (Gibco) staining prior to use.

Mouse Model of Hepatic Metastases, and Cell Migration

The MCA26 tumor line is a BALB/c-derived, chemically induced colon carcinoma with low immunogenicity [see, Corbett T H, et al. Tumor induction relationships in development of transplantable cancers of the colon in mice for chemotherapy assays, with a note on carcinogen structure. Cancer Res. 1975; 35(9):2434-9]. 14 days after tumor injection, when tumors were approximately 1×1 cm in size, mice were adoptively transferred monocytic MDSCs which had been cocultured for 4 hours with Ferridex® (ferumoxides, Berlex; Montville, N.J.) at a concentration of 11.2 μg/ml and subsequently stained with PKH26 membrane linker dye per manufacturer specifications. Mice were sacrificed daily and spleen, bone marrow, lymph nodes, liver, lung, and tumor were harvested. Organs were homogenized into single cell suspensions, and immune cells were isolated via percoll density gradient. Fraction 2 was collected, stained for MDSC markers, and analyzed via FACS for PKH26 positivity. Other murine organs were harvested and fixed with O.C.T. compound (Tissue-Tek; Torrence, Calif.) at various time points. Organs were then sectioned and stained with Perl's Prussian blue to identify the presence of iron.

Melanoma Tumor and Metastases Models

The B16 tumor cell line (ATCC CRL-6475™) is a C57BL/6-derived melanoma cell line with low immunogenicity. The ovalbumin (OVA)-expressing B16 tumor line used is a stable OVA-transfected clone in order to track tumor antigen specific T cell responses in vivo. TC-1 was derived from the primary lung epithelial cells of C57BL/6. The HPV E6/E7-expressing TC-1 tumor cells were generated to test the efficacy of various E6/E7-specific vaccines. To establish a tumor model of metastatic lung cancer and liver cancer, C57Bl/6 mice were challenged with $3 \times 10^5$ tumor cells intravenously or implanted with $7 \times 10^4$ tumor cells intrahepatically.

In the intrahepatic OVA-B16/C57BL/6 tumor model, when tumors reached the size of $5 \times 5$ mm$^2$ or, for the OVA-B16 lung metastatic tumor model, in mice with existing tumors, $5 \times 10^6$ MDSCs loaded with nanoparticles were adoptively transferred into these tumor bearing mice. Survival of test mice was determined. For some experiments, mice were sacrificed after adoptive transfer of MDSC after 14 days. The proliferation of purified splenic T cells and lung lymphocytes in response to OT-I OVA peptide, OT-II OVA peptide or OVA protein (5 mg/mL) in the presence of irradiated naïve splenocytes was assessed. For sunitinib malate ((Sutent, Pfizer)) treatment, 0.015 mg/day was given daily for 28 days as clinical protocol. The TC-1 tumor model used the same protocol.

Ferumoxides Labeling and Uptake

MDSCs were cocultured for 4 hours with Ferridex (ferumoxide, Berlex; Montville, N.J.) at 11.2 mg/ml and sent to inductively coupled plasma mass spectrometry (ICP-MS, Cantest, Burnaby, BC) to determine total iron content. The percent ferumoxides uptake was then determined based upon the amount of iron detected in the cells by ICP-MS versus the total concentration of ferumoxides added during incubation. Cytospins were prepared by diluting $2 \times 10^4$ cells in 300 μL PBS. The cells were spun down on microscope slides using a Cytospin 3 centrifuge (Shandon, UK). Perl's staining was performed by fixing the samples with 4% paraformaldehyde for 10 minutes followed by incubation with 2% potassium ferrocyanide in 2% hydrochloric acid. The slides were washed with distilled water and counterstained with nuclear fast red and dehydrated in ethyl alcohol (90, 95, and 100%).

Images were acquired with a Nikon microscope using specialized software (SOFT, Diagnostic Instruments, MI). The location of the ferumoxides within the cell was then evaluated using Transmission Electron Microscopy (TEM, model CX-100; JEOL, Toyko, Japan), according to established protocols.

In Vitro Magnetic Resonance (MR) Imaging of Ferumoxides Labeled Cells

In vitro cell phantoms were prepared by adding known numbers of ferumoxides-labeled MDSCs into 0.2-ml warm 2% agarose gel in 0.5-ml plastic tubes. Samples were mixed and snap frozen in dry ice to allow for a homogenous distribution of cells within the gel. All phantoms were then imaged at 9.4 Tesla using a 89 mm bore system operating at a proton frequency of 400 MHz (Bruker Instruments, Billerica, Mass.). The same 30 mm mouse coil used for in vivo imaging was also used for phantom testing. In order to evaluate the MR signal (as the effective transverse relaxation rate, $R2^*$) as a function of cell number and ferumoxides concentration multi-echo gradient echo (GRE) sequences were applied with the following parameters: TR=29.1 ms, TE=5.1 ms to 10 ms (n=5), 30 slices, flip angle=30°, number of signal averages (NEX)=8, in-plane resolution=0.098 $mm^2$, and 100% z-rephasing gradient. $R2^*$-maps were generated on a pixel-by-pixel basis using a custom Matlab program (The Mathworks, R2007b, Boston, Mass.). The signal intensity associated with each pixel was normalized to the standard deviation of adjacent noise prior to linear fitting of the signal-to-noise ratio versus echo time (TE). For the GRASP sequence, all sequence parameters were equivalent to those used for the GRE sequence except that the z-rephasing gradient was reduced to 50%.

In-Vivo Detection by MRI

Tumor bearing BALB/c mice (n=7) were administered $5 \times 10^6$ ferumoxides-labeled MDSCs via tail vein injection. MR images of the liver, spleen and tumor were obtained immediately prior to injection and over a 1 week time interval post injection. All in-vivo MR imaging was performed at 9.4 Tesla using the pulse sequence parameters described for the ex-vivo phantom. A respiratory gating system (SA Instruments, Inc., Stony Brook, N.Y.) was used to gate the sequences and monitor the animals during imaging. R2 and $R2^*$-mapping was performed on a pixel-by-pixel basis using a Matlab program, as described. Additionally, to account for tumor growth over the 4 day time interval, the signal-to-noise ratios (SNR, where SNR=signal intensity divided by the standard deviation of the noise) were divided by the tumor area ($mm^3$) for all data obtained using GRE sequences Immediately after the last MR scan, the mice were sacrificed, saline perfused, and the liver and tumor isolated. A section of tissue was stained for iron using Perl's Prussian blue and the remaining tissue was re-weighed. The liver was sent to relaxometry and the tumor sent to ICP-MS for the determination of iron content.

Iron Content in Liver and Tumor-Relaxometry

Dose-response curves were generated by spiking ex vivo tissue homogenate with known concentrations of ferumoxides (0-1 mM Fe, n=6). The transverse relaxation times (T2) were determined at 60 MHz (40° C.) using a Bruker Minispec spectrometer (Bruker Medical GmbH, Ettlingen, Germany). T2 values were calculated based upon a mono-exponential fit of echo amplitude versus time. The following relationship between the transverse relaxation rates (denoted as y) and ferumoxides concentration (denoted as x) was observed for the spiked samples: for the liver homogenate y=246x+14 ($R^2$=0.997). The limit of quantification was determined as 0.038 mM Fe.

Recombinant Vesicular Stomatitis Vectors and Transwell Assay

The construction of rVSV-GFP and rVSV(MΔ51)-M3 has been described previously [see, Ebert O, et al. Oncolytic vesicular stomatitis virus for treatment of orthotopic hepatocellular carcinoma in immune-competent rats. Cancer Res. 2003; 63(13):3605-11; Wu et al., 2008, supra]. $1 \times 10^4$ tumor cells were cultured for 24 hours in the lower stage of a 24 mm transwell plate (Corning Costar). MDSCs were isolated as previously described and placed into VP-SFM medium (Gibco®) on ice with rVSV-MDSC at various MOIs for 4 hours. After this time, cells were washed with ice cold PBS 3-5 times and $1.5 \times 10^5$ cells were placed in the upper stage (0.4 µm pore size). Plates were cultured for 24 hours and analyzed with a Leica DMRA2 fluorescent microscope.

Therapeutic Protocols

Metastatic colon cancer was induced as described previously [see, Caruso M, et al. Adenovirus-mediated interleukin-12 gene therapy for metastatic colon carcinoma. Proc Natl Acad Sci USA. 1996; 93(21):11302-6]. 8-9 days after tumor injection, tumor size was examined, and mice with tumors $5 \times 5$ mm-$6 \times 6$ mm were adoptively transferred $5 \times 10^6$ monocytic MDSCs which had been cocultured in VP-SFM media (Gibco) with rVSV-GFP for 4 hours on ice at an MOI of 100 in the presence of 1× polybrene (hexadimethrine bromide, Millipore; Billerica, Mass.). Cells were washed with ice cold PBS three times and adoptively transferred via tail vein injection. $Ly6C^-$ cells were treated similarly prior to adoptive transfer. $5 \times 10^7$ pfu rVSV-GFP was resuspended in 250 µl PBS and injected via tail vein. To conjugate antibody to virus particles, anti-VSV-G antibody was incubated on ice in the presence of rVSV-GFP or rVSV(MΔ51)-M3 (MOI: 1000) and polybrene for 1 hour and then $5 \times 10^6$ MDSCs or $Ly6C^-$ cells were added and incubated on ice for 1 more hour prior to washing and transfer. Mice were monitored daily for therapeutic side effects and were sacrificed when their tumors reached sizes large enough to cause severe disability. Upon sacrifice, tumors and spleens were harvested. Tumors were fixed in 4% paraformaldehyde and stained for VSV-G antigen (Alpha Diagnostic; San Antonio, Tex.).

Cell Migration Comparison

MDSCs were isolated as above from CD45.1 C57BL/6 tumor bearing mice. CIK cells were isolated per established protocols (see, Thorne et al. (2000) *Science* 311(5768):1780-1784) from CD45.1 mice. T-cells were isolated from the spleens of tumor bearing CD45.1 C57BL/6 mice via staining by Thy1.2-FITC, and separated using anti-FITC microbeads via an AutoMACS cell sorter. Activated T-cells were isolated similarly and cultured with IL-2 at 200 U/ml (Peprotech; Rocky Hill, N.J.) for 3 days. Macrophages were isolated by culturing bone marrow of naïve CD45.1 mice for 7 days with MCSF (Peprotech) at 30 ng/ml, attached cells were harvested. Dendritic cells were isolated by culturing bone marrow of naïve CD45.1 mice for 7 days with 1% GMCSF conditioned medium (from J558L cell line), suspended cells were harvested. Monocytes were isolated from percoll fraction 2 from the bone marrow of naïve CD45.1 mice. Cells were adoptively transferred to CD45.2 C57B1/6 mice bearing intrahepatic LLC tumors 14 days after tumor implantation via tail vein. Mice were sacrificed after 72 hours, organs were homogenized to single cell suspensions, CD45.1 cells were stained, and analyzed via FACS.

$TCID_{50}$ Analysis of Viral Binding

Organs and cells were lysed using a TissueLyser (Qiagen, Valencia, Calif.). Cell lysates were serially diluted and aliquots were incubated with BHK21 cells at 37° C. in VP-SFM medium for 72 hours. Cells were then examined under light microscopy for cytopathic effects (CPE). $TCID_{50}$ concentration was determined employing the Spearman-Karber method, described in Wechsler and Luedke (1991) *J Clin Microbiol.* 29(1): 212-214.

qPCR

RNA was isolated from organs using Trizol (Invitrogen; Carlsbad, Calif.) per manufacturer's specifications. DNA was digested with DNAse I (Invitrogen) cDNA was made from RNA using RT2 First Strand Kit (Qiagen; Valencia, Calif.) and qPCR was performed in 384-well plates using RT2 Real-Time SYBR Green/Rox PCR master Mix (SABiosciences; Frederick, Md.) on an ABI PRISM 7900HT (Applied Biosystems; Foster City, Calif.) using the following primer sequences: 5'-TTCTTGGTTCTCCGAGTTGG-3' (SEQ ID NO: 1) and 5'-AACAGGAGGATGCAGCATTT-3' (SEQ ID NO: 2).

Cytotoxicity Assay

MDSCs cultured in the presence or absence of VSV-G Ab and rVSV(MΔ51)-M3 as above (MOI:300) in the presence of polybrene and coincubated with LLC tumor cells at 12.5:1, 25:1, 50:1, and 100:1 for 4 hours. Supernatants were collected for measurements of Lactate Dehydrogenase (LDH) release (CytoTox 96 Non-Radioactive Cytotoxicity Assay Kit; Promega, Madison, Wis.). Specific killing (in percentage) was calculated as experimental LDH release/maximum LDH release.

Peptides and Nanoparticles

OT-I OVA peptide, OT-II OVA peptide, OVA protein were purchased from AnaSpec (Fremont, Calif.). HPV E6 peptide EVYDFAFRDL (48-57) (SEQ ID NO: 3) and HPV E7 peptide RAHYNIVTF (49-57) (SEQ ID NO: 4) (GENSCRIPT USA, INC (Fremont, Calif.)). Aluminum peroxide nanoparticles were synthesized by Dr. Hong-Ming Hu (Portland). The aluminum peroxide-based nanoparticles ($\alpha$-$Al_2O_3$ nanoparticles) used are described in detail in Li et al. (2011) Nat Nanotechnol 6(10):645-50. The aluminum peroxide nanoparticles (NP) were conjugated to OVA and added at a concentration of 10 µg/ml of OVA-NP to $10 \times 10^6$ MDSCs/ml.

Preparation of MDSCs for Nanoparticle Experiments

Mice with tumor sizes greater than $10 \times 10$ $mm^2$ were sacrificed and the spleens, tibias, and femurs were harvested. After lysis of red blood cells (RBCs), bone marrow cells and splenocytes were cultured overnight. On the second day, loosened attached cells were harvested and fractionated on a Percoll (GE Healthcare, Piscataway, N.J.) density gradient. MDSCs were purified from the cells fraction at 50%-60% by anti-CD115-PE or antiLy6C-PE and anti-PE microbeads (Miltenyi Biotec, Auburn, Calif.). The purity of the sorted cell populations was >95% homogeneous CD11+/Gr-1+, as determined by flow cytometry. The purified MDSCs were treated with PGN (peptidoglycan, Sigma) and/or sunitinib malate for 2 days or loaded with various nanoparticles for 12 hours and then adoptively transferred into test mice.

MDSC Suppression Assay

The suppressive activity of MDSC was assessed in a peptide-mediated proliferation assay of TCR transgenic T cells as described previously. See, Huang B, et al (2006) *Cancer Res.* 15; 66(2): 1123-31. Purified CD4+ T cells from naïve OT-II transgenic mice were co-cultured with MDSCs isolated from spleen of WT or various knockout tumor-bearing mice at a ratio of 4:1 (T cell/MDSC) in the presence of recombinant murine OT-II OVA peptide (0.25 mg/mL, R&D Systems). PGN (1 mg/ml) and/or sunitinib malate (250 nM) were added to the medium. After a 5-day stimulation, cells were harvested and stained with anti-CD4-FITC, anti-CD25-PE-Cy7, anti-Tbet-PerCP-Cy5.5, anti-RORγt-APC and anti-Foxp3-PE, or isotype control (eBioscience).

T Cell Priming

Thy1.2+ T cells were purified from naïve mice and co-cultures with purified CD115+ MDSCs were treated with nanoparticle alone (NP), nanoparticle-conjugated with OVA (NP-OVA), and nanoparticle conjugated with OVA and PGN.

Cytokine Detection by ELISA

Cytokine ELISAs were done on culture supernatants using the mouse TNFa, IL-10, IL-13, Interferon γ (IFN-γ), IL-17 ELISA kits (R&D Systems) according to the manufacturer's instructions.

T Cell Proliferation Assay

The sorted splenic Thy1.2+ T cells ($2 \times 10^5$) with irradiated (2,000 rad) naïve splenic cells ($1 \times 10^4$) as APC or were co-cultured with or without OT-I OVA peptide, OT-II OVA peptide, OVA protein, or HPV E6 and E7 peptide (5 mg/mL) in 96-well microplates. [$^3$H]thymidine was added during the last 8 hours of 72-hour culture.

Cytotoxic T Lymphocyte Assay and Macrophage-Dependent Cytotoxic Assay

Purified splenic Thy1.2+ T cells from OVA-B16-tumor bearing mice or TC-1-tumor bearing mice in metastatic model were re-stimulated with 5 mg/ml OVA peptide or 5 mg/ml HPV type 16 E6/E7 peptides (HPV E6 peptide: EVYDFAFRDL (48-57) (SEQ ID NO: 3) and HPV E7 peptide RAHYNIVTF (49-57) (SEQ ID NO: 4) (GENSCRIPT USA, INC (Fremont, Calif.)). See also, Martini et al. (2007) *Vaccine* 25(17):3302-10), in the presence of irradiated splenocytes for 3 days. Lung F4/80+ macrophages from TC-1-tumor bearing mice in the metastatic model were purified with anti-F4/80 PE and anti-PE microbeads. Activated T cells or purified F4/80+ macrophages were co-incubated with IFN-γ treated B16-OVA or TC-1 tumor cells (target cells) at 12.5:1, 25:1, 50:1 and 100:1 for 4 hr. Supernatants were collected for measurement of lactate dehydrogenase (LDH) release (Cyto-Tox96 Non-Radioactive Cytotoxicity Assay Kit, Promega). Specific killing (in percentage) was calculated as experimental LDH release/maximum LDH release as follows: % cytotoxicity=100 (experimental release–effector spontaneous release–target spontaneous release)/(total target release–target spontaneous release).

Statistical Analysis

One-way ANOVA with Bonferroni post hoc tests was used to evaluate the significance associated with change in R2* values as a function of time post injection. Student's t-test was used to compare the differences in tumor sizes and weights. The log rank test was used to determine the significance of survival data. For samples with equal variance, the paired Student's t test for equal variance was used. For samples with unequal variance, Wilcoxian signed-rank test was used for statistical analysis. $p < 0.05$ was considered to be statistically significant.

Example 1

Labeling of MDSCs with Iron Oxide Particles

This Example demonstrates that adoptively transferred MDSCs can be effectively labeled by co-culturing MDSCs in the presence of ferumoxides, an FDA approved SPIO (Feridex IV®) already in use for in vivo clinical cell tracking in the United States and Europe, and that labeled MDSCs migration can be tracked.

To identify the in vivo trafficking patterns of adoptively transferred MDSCs in a longitudinal manner within a single mouse, diagnostic imaging methods were employed. Recently several groups have used superparamagnetic iron oxide particles (SPIOs) to label a variety of different cells which they could then follow via MRI [see, Arbab A S, et al. (2004) *Blood* 104(4):1217-23; Hamm J, et al. *NMR Biomed.* 2008; 21(2):120-8; Beduneau A, et al. *PLoS One.* 2009; 4(2): e4343]. These techniques were adapted to label MDSCs with ferumoxides, which enabled detection, using MRI, of the presence of labeled MDSCs within the tumor and other organs as a function of time post injection without the need to sacrifice the animals for FACS analysis of isolated cells. Another benefit of MRI imaging, as carried out in this Example, is the ability to visualize exactly where in each organ the labeled cells have migrated.

MDSCs were isolated from the spleens and bone marrow of tumor-bearing mice. First cells underwent percoll fractionation to select monocytic cells, and then monocytic MDSCs were selected from this population using antibodies targeting Ly6C. More than 90% of this population was $CD11b^+GR1^+$, the classical markers of MDSCs. Cytospin, followed by prussian blue staining of these cells showed that >90% of MDSCs cocultured with ferumoxides stained positive for iron. Next MRI phantoms of known iron concentration were created and numbers of MDSCs in agar gel were analyzed via MRI. From these phantoms a linear relationship between cell number and MRI signal loss was observed ($R2=0.9251$) (FIG. 1).

Example 2

MDSCs Migrate to Tumors In Vivo

This Example demonstrates that adoptively transferred, labeled MDSCs migrated to tumor sites in vivo.

Figure 2A:
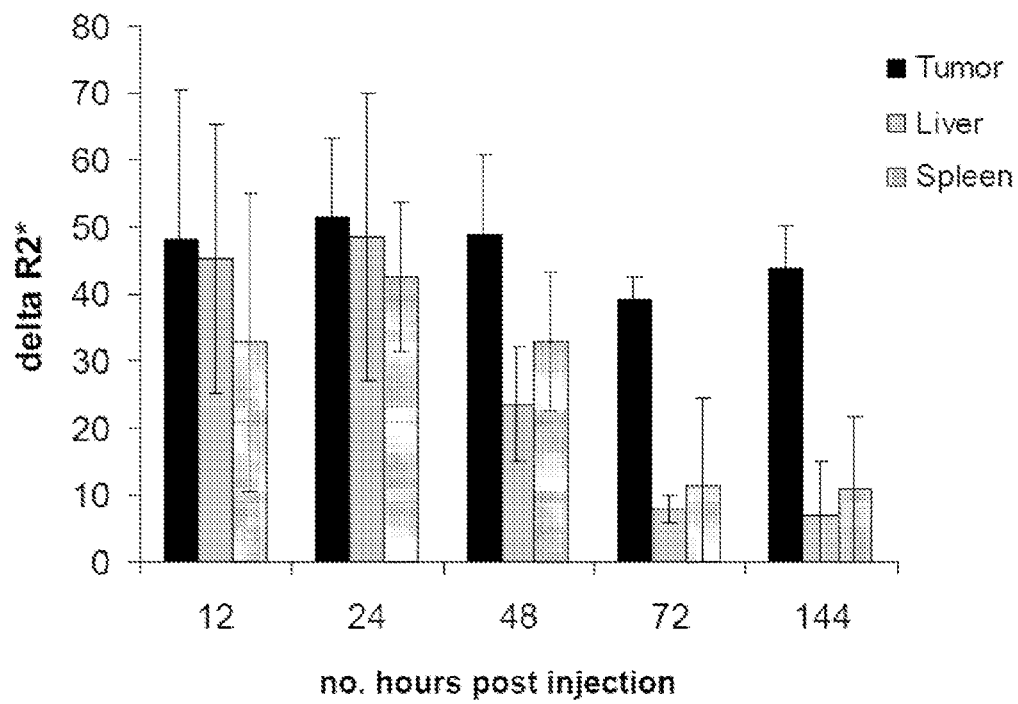
FIG. 2A is a graph showing the R2* quantification of MRI data performed pixel-by-pixel to quantify signal loss as a function of time in the livers of mice injected with ferumoxides-labeled MDSCs. Data is represented as an increase in signal loss over baseline (pre-transfer values) at the indicated time points.

Ferumoxides-labeled MDSCs were administered to mice that had previously been injected intrahepatically with MCA26 colon cancer cells to simulate hepatic metastases of colorectal cancer, and followed over one week post injection. Mice received MRIs prior to MDSC transfer and then daily (n=7). T2*-weighted images (GRE images) and GRASP images were obtained and analyzed. At day 3 after transfer increased signal loss was observed within the tumor, highlighting both the periphery of the tumor as well as vascular structures. White marker sequences such as GRASP have been developed to increase the accuracy of labeled cell detection [see, Mani V, et al. Gradient echo acquisition for superparamagnetic particles with positive contrast (GRASP): sequence characterization in membrane and glass superparamagnetic iron oxide phantoms at 1.5 T and 3 T. Magn Reson Med. 2006; 55(1):126-35]. In this sequence the z-rephasing gradient is reduced so that dipolar fields generated by the iron-laden cells are re-phased and positive signal is observed. Good correlation between GRE and GRASP was observed. The relative change in the R2* values, indicate maximum uptake of the cells into the lesion 3 days post injection (39±2% Injected Dose (ID), as determined by ex vivo ICP-MS), as shown in FIG. 2A.

Figure 2B:
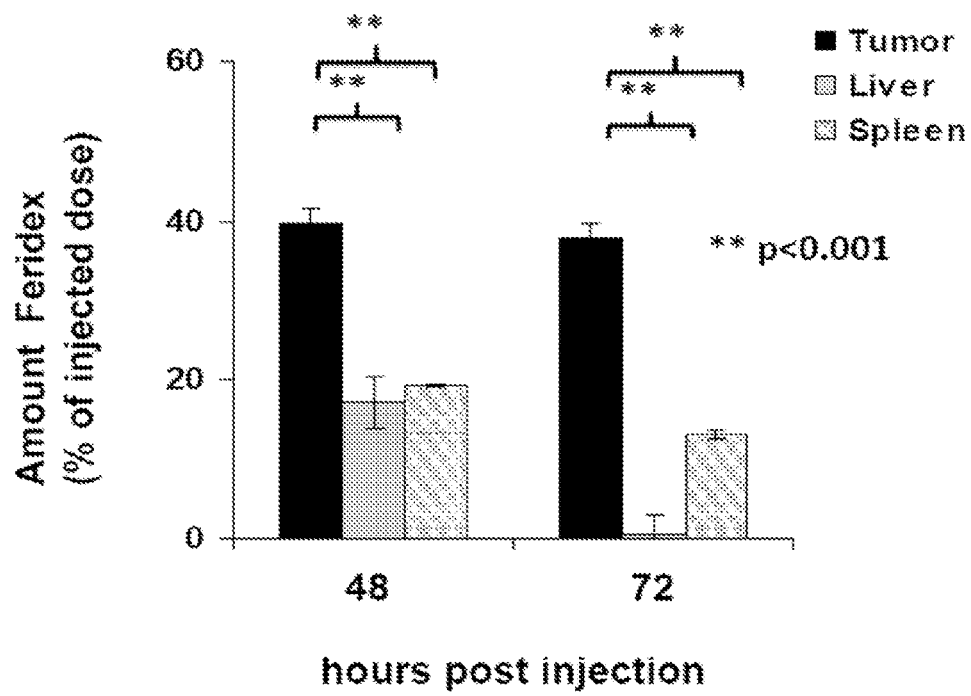
FIG. 2B is a graph quantifying the amount of ferumoxides present in the indicated tissues (tumor, liver or spleen), expressed as the percent of initial injected dose of ferumoxides, at the indicated time points post injection of ferumoxides-labeled MDSCs (**$p<0.001$).

Due to the high endogenous concentration of iron in the liver, ICP-MS cannot be used to evaluate in vivo ferumoxides iron concentrations. Relaxometry, an NMR technique which is able to separately identify superparamagnetic iron from physiologic iron, was therefore used to determine the concentration of ferumoxides within the tissue. The contribution of the endogenous paramagnetic iron to the dipolar transverse relaxation times (T2) is minimal (<5%) compared to that of ferumoxides [see, Briley-Saebo K, et al. Hepatic cellular distribution and degradation of iron oxide nanoparticles following single intravenous injection in rats: implications for magnetic resonance imaging. Cell Tissue Res. 2004; 316(3): 315-23]. Mice were sacrificed, saline perfused, and tumor, liver and spleen were removed. The presence of ferumoxides was determined by ICP-MS (tumor, spleen) or relaxometry (liver) and results were compared to the known amount of ferumoxide injected into the mice based on the standard curve determined in FIG. 1. Only limited liver and spleen uptake (17±1% ID) was observed, while significant increases in iron uptake in the tumors was observed at both 48 hours and 72 hours post injection of ferumoxide-labeled MDSCs, indicating that the tropism of MDSCs specifically delivered ferumoxide to tumor cells (FIG. 2B). Perl's staining confirmed the presence of iron within the transferred cells at 3 days post injection. The observation that the labeled MDSCs migrated to the lesion and contained the ferumoxides demonstrated that MDSCs are able to reach the tumor with limited phagocytosis and limited metabolism of the ferumoxides label.

In order to evaluate the ability of in vivo R2* values to predict the ferumoxides concentration in the liver and spleen, calibration curves were constructed to compare the in vivo R2* values to the ex vivo ferumoxides concentrations (obtained either by relaxometry or ICP-MS). The resultant correlation coefficient, associated with a linear fit of the data (n=10 data points) was $R2=0.7022$. The detection limit of the method was 0.031 mM Fe (approximately 7% the injected dose). As a result, in vivo R2* values may be used to approximate ferumoxides concentrations in tissue as long as the tissue concentrations are greater than 0.031 mM Fe. At lower concentrations, signal loss may be observed, but in vivo R2* values may not be used to approximate ferumoxides concentration. Employing these methods it was reliably shown using MRI cell tracking, that adoptively transferred MDSCs target tumor sites, arriving 2-3 days after transfer, and distributing themselves peripherally and perivascularly.

Figure 3A:
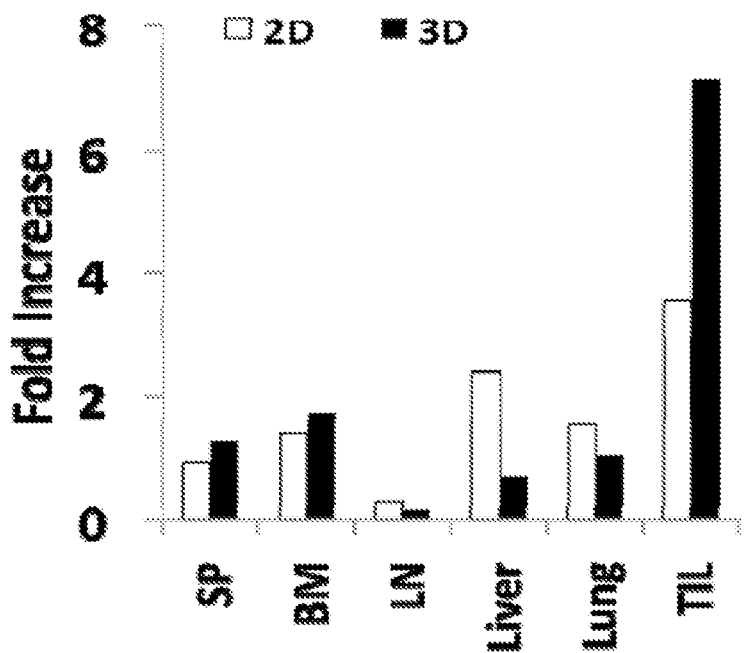
FIG. 3A is a graph showing the fold increase in PKH26 positivity over background signal (determined from mice not receiving PKH26-labeled MDSCs) at 2 days ("2 D") and 3 days ("3 D") post MDSC transfer in the indicated tissues ("SP"=spleen; "BM"=bone marrow, "LN"=lymph nodes, "TIL"=tumor).
Figure 3B:
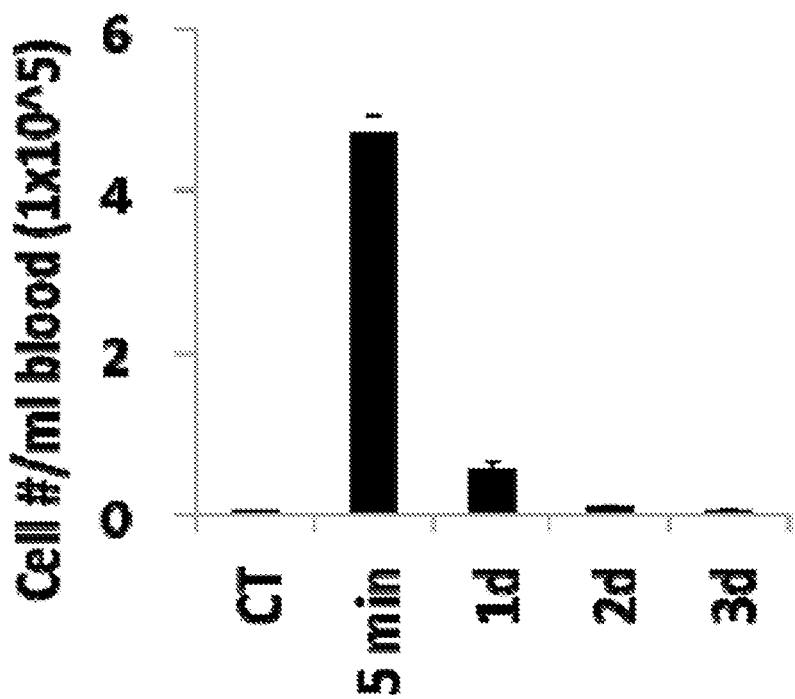
FIG. 3B is a graph showing the number of circulating labeled MDSCs, expressed as the number of cells×$10^5$ per ml blood, in mice injected with PKH26-labeled MDSCs (Ly6C$^+$ PKH26$^+$ cells) at the indicated time points ("CT"=control (background) "min"=minutes, "d"=day(s)).

Flow cytometry was used to confirm the MRI findings. Following selection, MDSCs were labeled with the red membrane linker dye, PKH26, and adoptively transferred to BALB/c mice which had previously been injected intrahepatically with MCA26 tumor cells. Mice were sacrificed daily, their liver, lungs, bone marrow, spleen, lymph nodes, blood, and tumors were harvested. Tumor were resected, homogenized, and immune cells were isolated via percoll extraction, stained with antibodies against Ly6C, and analyzed via FACS for PKH26 positivity (n=3 per time point). FACS analysis of these cells showed an increase in PKH26 signal in the tumor to 4 times over background two days after adoptive transfer. This level peaked at 8 times background at day 3 and was falling by day 4 after transfer. This corresponded to an increase in splenic PKH26 signal on day 4 to twice its previous level, likely corresponding with clearance of transferred cells by the spleen at this time. Little increase in PKH26 signal was observed in the other lymphoid rich organs at any time points. Notably, the liver showed no increase in signal despite its proximity to the tumor site. FIG. 3A shows the fold increase in PKH26 positivity over background signal, determined from mice not receiving PKH26 labeled MDSCs, at 2 days and 3 days post MDSC transfer in the indicated tissues (n=3 per time point). Upon analysis of the blood after transfer, levels of circulating MDSCs dropped in correspondence to tissue distribution of MDSCs, with blood levels reaching their nadir 2 days after transfer (FIG. 3B) (n=2 per time point).

Example 3

MDSCs can Transfer Oncolytic Viruses to Tumor Cells In Vitro and In Vivo

This Example demonstrates the effectiveness of MDSCs for the delivery of tumor-specific therapeutics. To test the effectiveness of VSV-loaded MDSCs (VSV-MDSCs) for delivering virus to tumor cells, MDSCs were infected with rVSV-GFP, a replication competent VSV vector expressing green fluorescent protein [see, Ebert O, et al. Oncolytic vesicular stomatitis virus for treatment of orthotopic hepatocellular carcinoma in immune-competent rats. Cancer Res. 2003; 63(13):3605-11]. MDSCs were co-cultured with rVSV-GFP at varying multiplicities of infection (MOIs) (10, 300, 1000), washed numerous times to remove free virus from their presence, and seeded into the upper well of a transwell plate. The lower well contained MCA26 tumor cells in culture. After 24 hours plates were examined for both cytopathic effects (CPEs) and GFP expression. Cells exhibiting CPE were expected to express minimal GFP as they should have already lysed and released their GFP. MDSCs at all MOIs showed high levels of GFP expression with minimal CPE, indicating that the cells were taking up and translating the viral genome but had yet to succumb to the lytic effects of VSV infection at 24 hours. Tumor cells, however, showed both CPEs as well as GFP expression. While there was a high level of GFP expression at all MOIs, CPEs observed at 24 hours were the highest in the MOI 300 group. This effect can be attributed to surface bound VSV since the transwell assay limits the contact between infected MDSCs and tumor cells, and since MDSCs are not being lysed to release virus at this time point. To show the applicability of VSV in the treatment of different tumor types, this experiment was repeated using both 4T1 breast cancer cell line and Lewis Lung cancer cell line (LLC) with similar results.

To test the effectiveness and safety of VSV-MDSCs in vivo, the MCA26 metastatic colon cancer model was used. Tumors were measured and mice were injected with either $5\times10^6$ VSV-MDSCs or PBS 8 days after tumor inoculation. At day 20 after tumor injection, mice were sacrificed and tumors were measured and weighed. Mice receiving VSV-MDSCs had significantly smaller sized tumors than controls (410 mm$^3$ versus 1710 mm$^3$; p=0.04, FIG. 4A) and their tumors weighed significantly less (0.85 g versus 3.22 g; p=0.002, FIG. 4B).

Figure 4A:
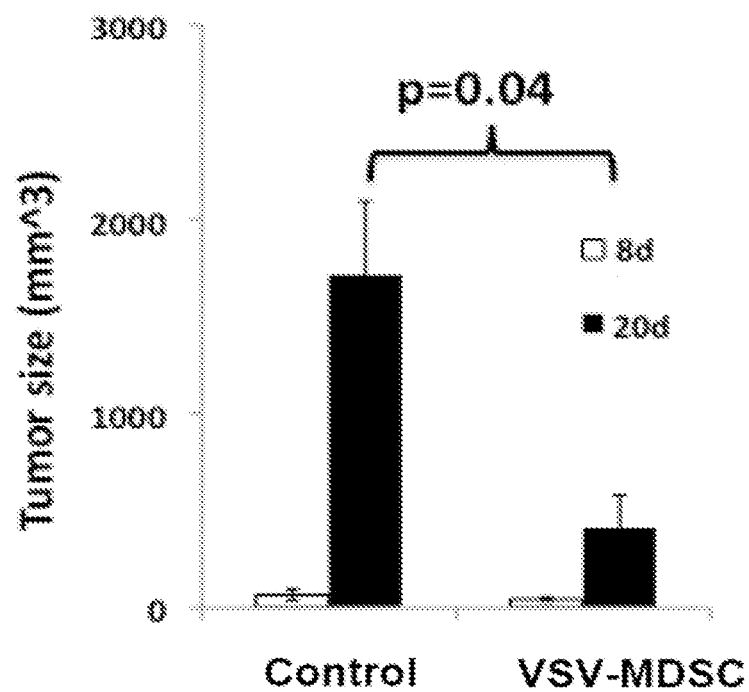
FIG. 4A is a graph showing tumor size in mice 8 days ("8 d") and 20 days ("20 d") after tumor injection, corresponding to the day (white bars) that the mice were injected with VSV-GFP-infected Ly6C$^+$ MDSCs and 12 days after VSV-MDSC injection (black bars), respectively, compared to PBS-injected mice ("control").
Figure 4B:
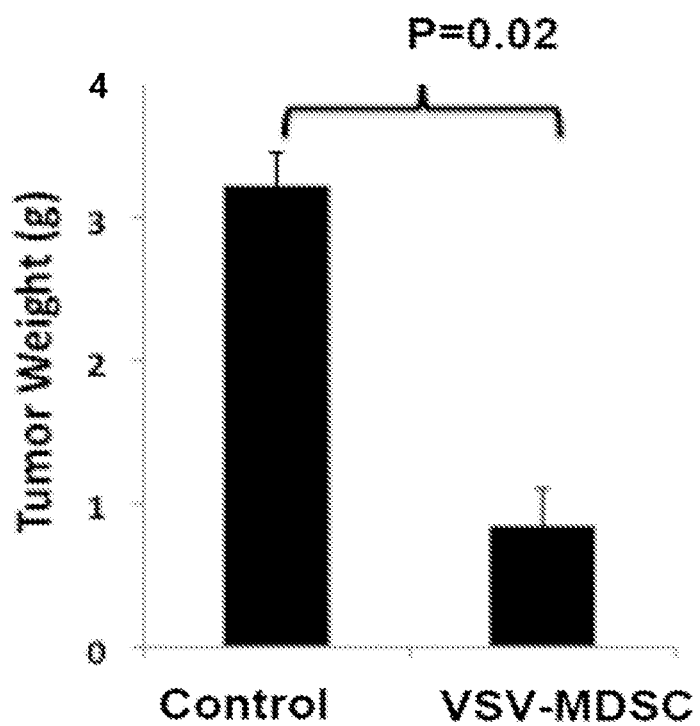
FIG. 4B is a graph showing tumor weight (g) in mice 12 days after VSV-MDSC injection compared to PBS-injected mice (control).
Figure 5:
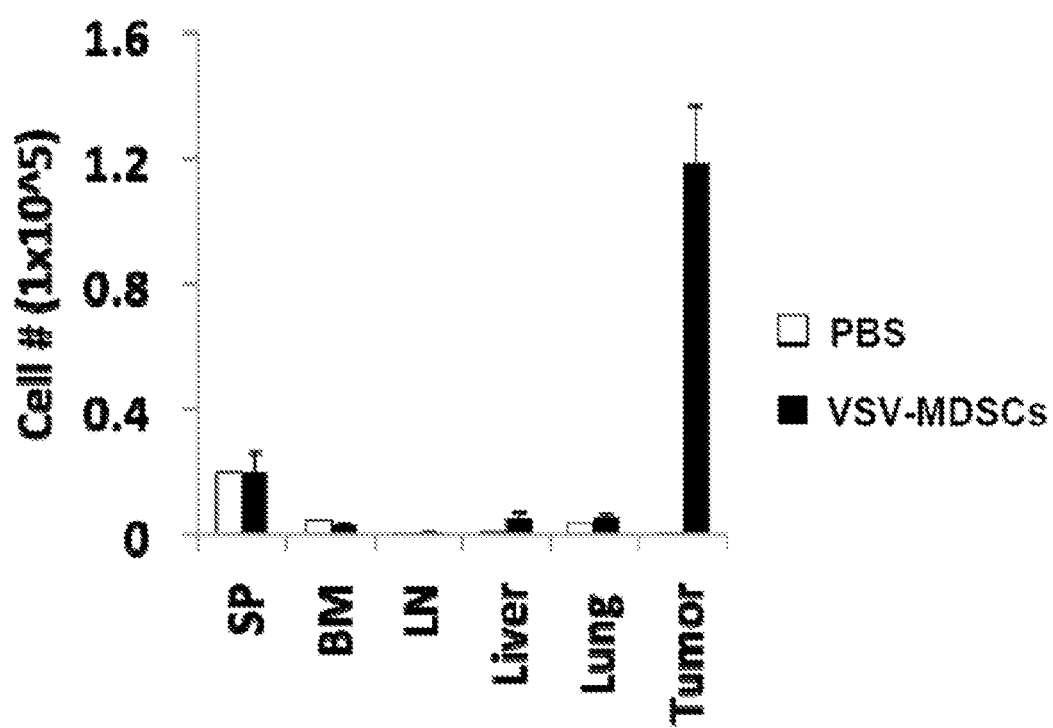
FIG. 5 is a graph showing the number of GFP$^+$ MDSCs expressed as number of cells×$10^5$ at the tumor site ("tumor") and in the indicated organs ("SP"=spleen, "BM"=bone marrow, "LN"=lymph nodes), 3 days after mice were injected with VSV-GFP-infected Ly6C$^+$ MDSCs ("VSV-MDSCs", black bars) or PBS (white bars).

None of the mice treated with VSV-MDSCs, however, suffered from neuropathic side effects sometimes associated with VSV therapy [see, Plakhov I V, et al. The earliest events in vesicular stomatitis virus infection of the murine olfactory neuroepithelium and entry of the central nervous system. Virology. 1995; 209(1):257-62], demonstrating the safety and efficacy of VSV-MDSC therapy. To confirm that VSV-MDSCs maintained their tumor specificity, the previous migration experiments using PKH26-labeled MDSCs (Example 2, FIGS. 3A and 3B) were repeated using VSV-MDSCs. Ly6C$^+$ MDSCs were infected with VSV-GFP (VSV-MDSC) and placed in the upper well of a transwell assay with MCA26 tumor cells plated in the lower well. Cells were incubated for 24 hours and examined under light and fluorescent microscopy for cytopathic effects and GFP expression. VSV-MDSCs (MOI: 300) were then adoptively transferred to intrahepatic MCA26 tumor-bearing mice 8 days after tumor injection. Mice were sacrificed 12 days later, tumors were removed, measured (FIG. 4A), and weighed (FIG. 4B) in comparison to tumor-bearing mice receiving only PBS injection ("control"). Mice that were injected with VSV-MDSCs had significantly smaller tumor sizes (mm$^3$) on day 20 after tumor injection compared to control mice (FIG. 4A, p=0.04). On day 20 after tumor injection, VSV-MDSC injected mice also had significantly decreased tumor weight compared to control mice (FIG. 4B, p=0.02). A large increase in the number of VSV-MDSCs at the tumor site was observed on day 3 after transfer, compared to both the background as well as other organs, indicating that infecting MDSCs with VSV does not alter their affinity for tumor sites, and that VSV-loaded MDSCs effectively target tumors (FIG. 5).

Example 4

Figure 6:
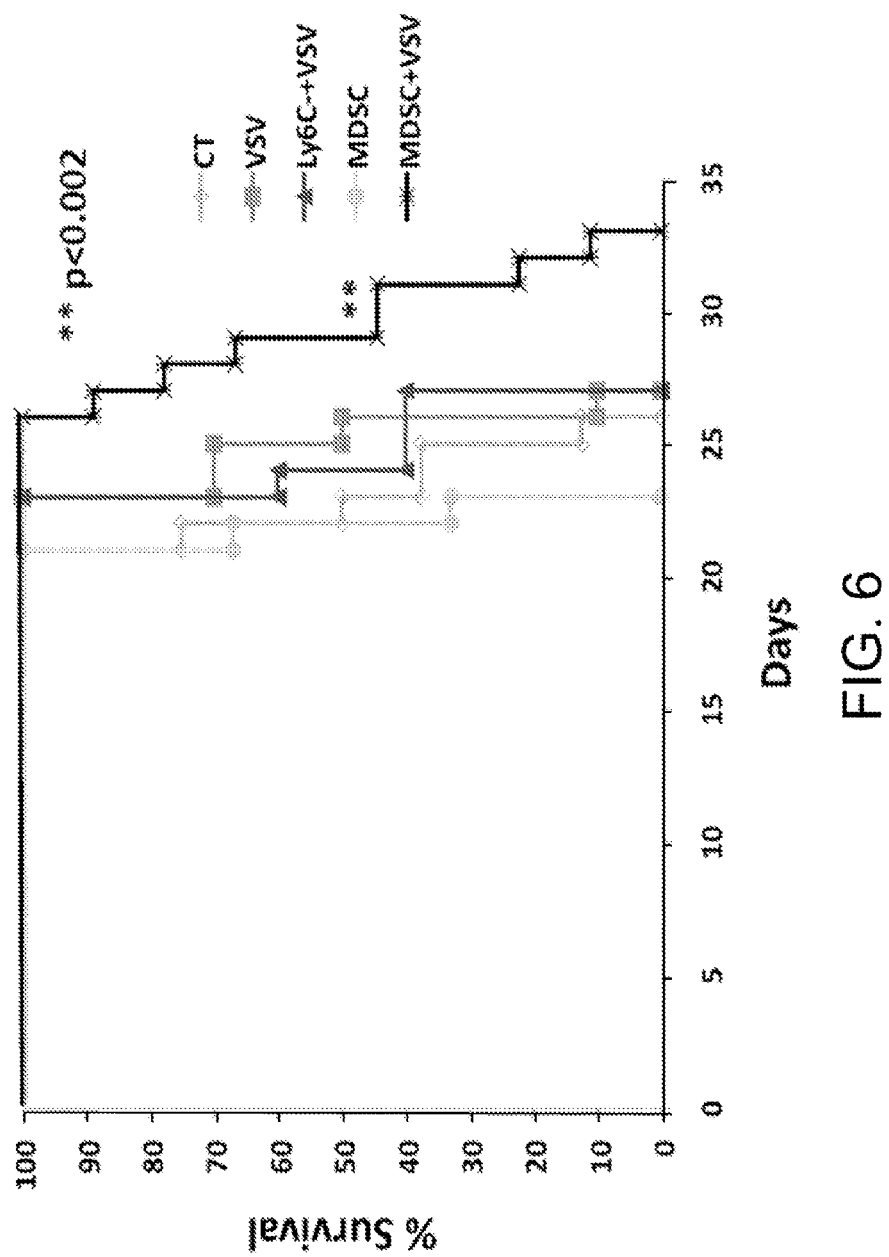
FIG. 6 is a Kaplan-Meier survival curve showing that VSV-infected MDSCs significantly prolonged survival in mice having intrahepatic MCA26 tumors in comparison to controls (**=$p<0.002$) ("CT"=PBS injection; "VSV"=peripheral injection of VSV alone; "Ly6C$^-$+VSV"=non-MDSCs infected with VSV; "MDSC"=uninfected MDSCs; "MDSC+VSV"=VSV-infected MDSCs).
Figure 7A:
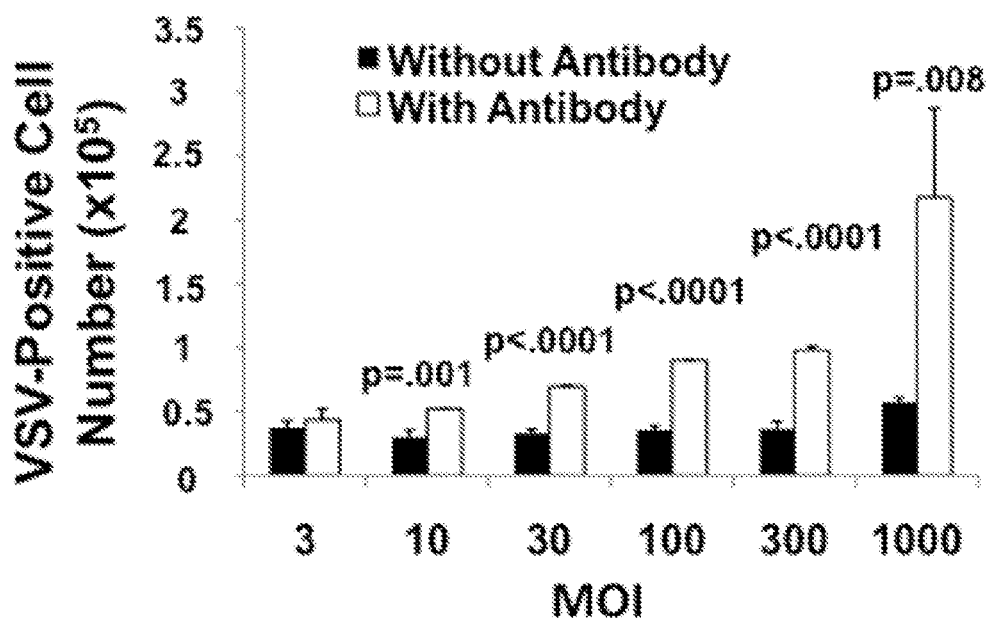
FIG. 7A is a graph showing the number (×$10^5$) of VSV positive cells in MDSCs combined with VSV-GFP at the designated MOIs, which had been incubated in the presence or absence of VSV-G antibody and cultured for 72 hours, followed by VSV-G staining and FACS analysis.
Figure 7B:
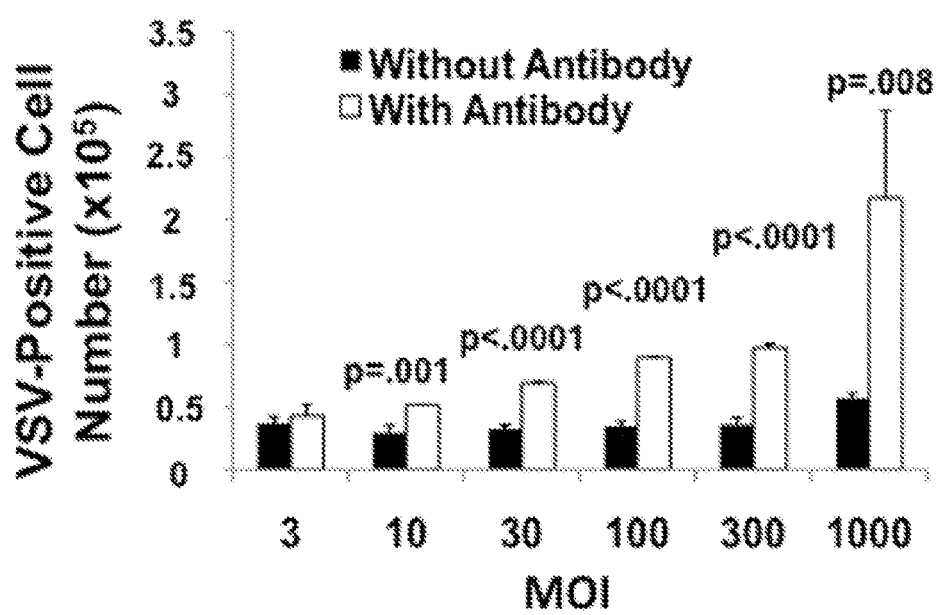
FIG. 7B is a graph showing the number of viral particles per 5×10^6 cells ($Log_{10}$) in MDSCs treated as in FIG. 7A at an MOI:300 and lysed and cultured with BKH21 cells for 72 hours, then analyzed for CPE and $TCID_{50}$.
Figure 7C:
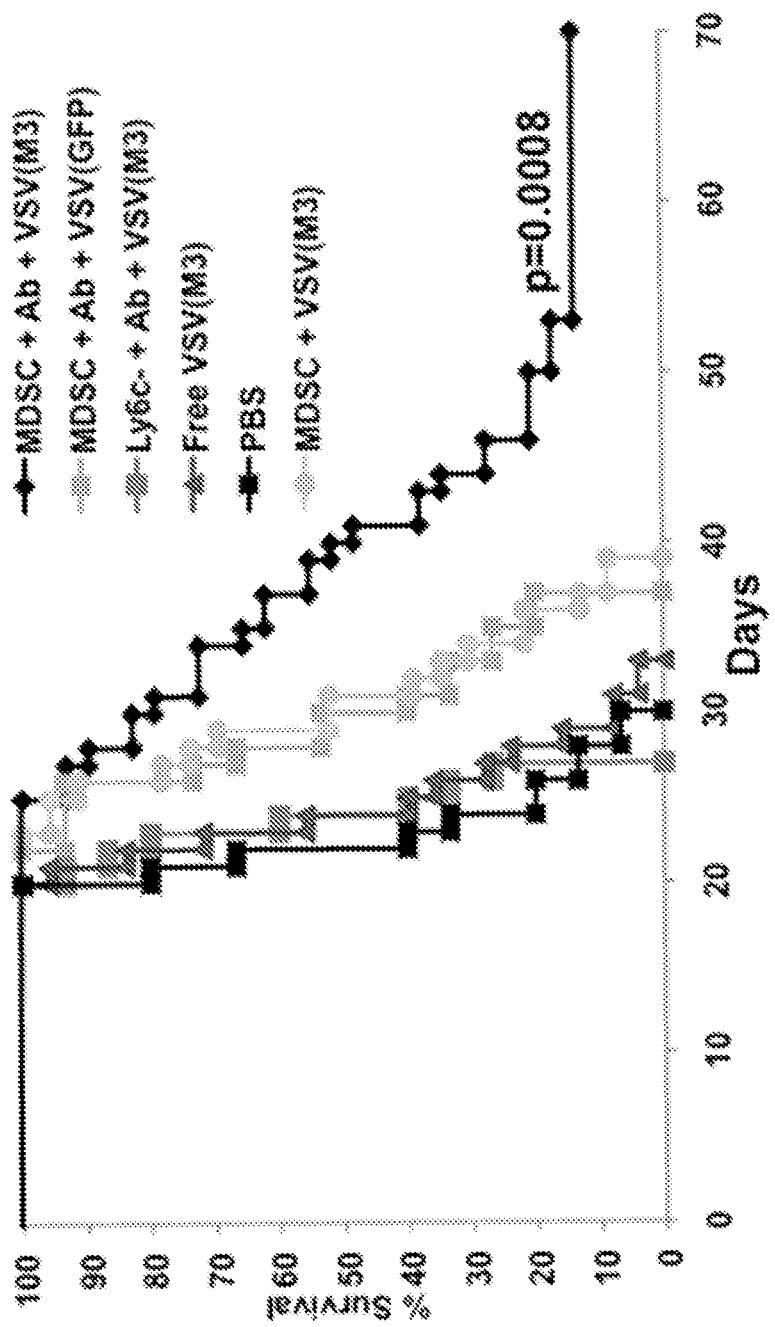
FIG. 7C is a Kaplan-Meier survival curve for intrahepatic MCA26 tumor-bearing mice that were followed for survival after treatment with MDSCs+antibody (Ab)+VSV(M3), MDSC+Ab+VSV (GFP), Ly6C+Ab+VSV (M3), PBS, or MDSC+VSV (M3) (MOI: 300; n=15); p values indicate statistical significance.
Figure 8:
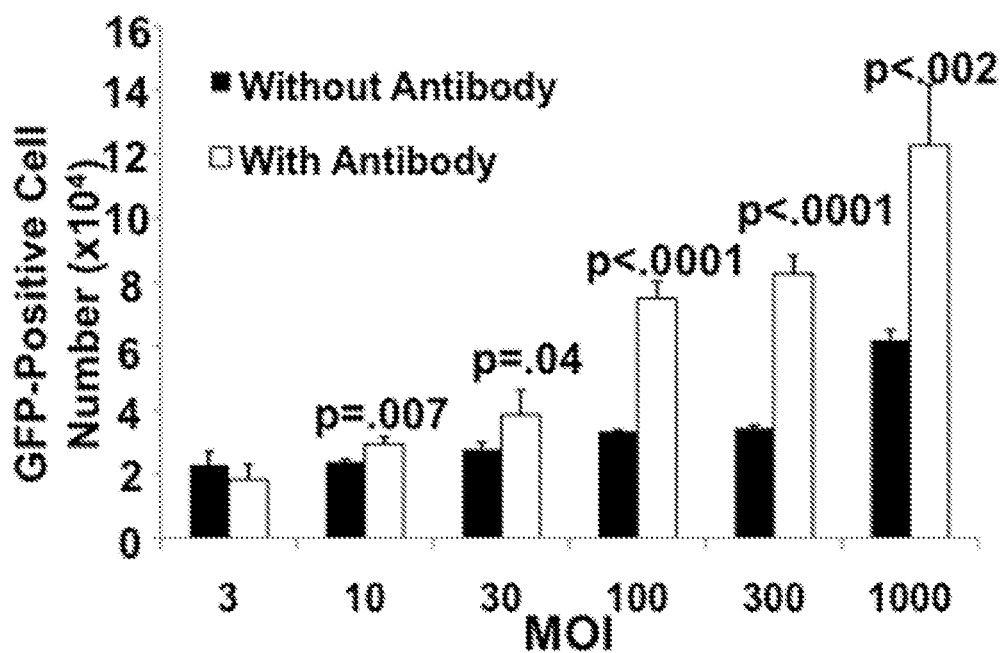
FIG. 8 is a graph showing the number of MDSCs (×10^4) staining positive for GFP following treatment with rVSV-GFP in the presence or absence of non-neutralizing anti VSV G-protein antibody at the indicated MOI.
Figure 9:
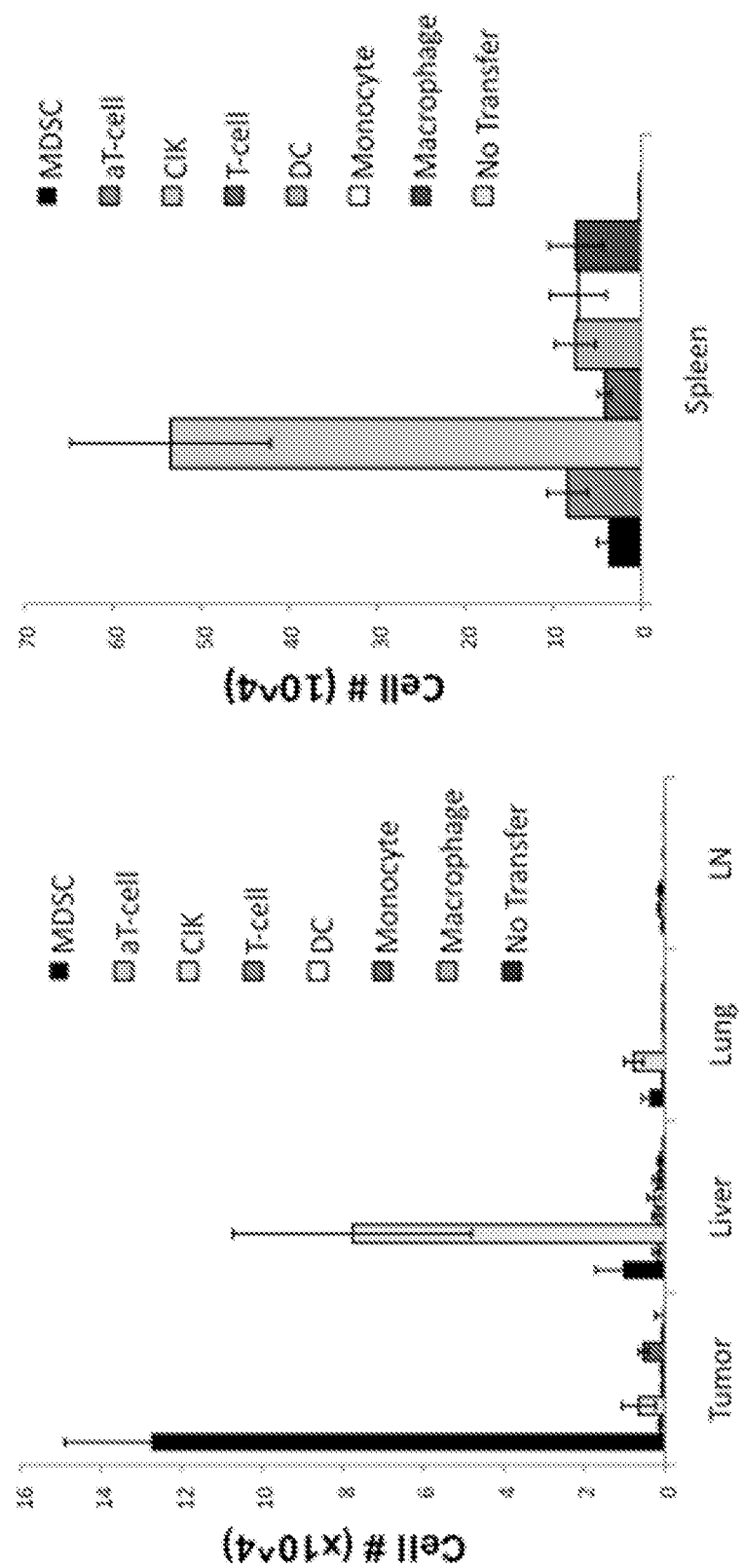
FIG. 9 contains graphs quantifying the number (×10^4) of each of the indicated cell types (CD45.1 Ly6C+ MDSCs (MDSC), Cytokine-induced killer cells (CIK), activated T-cells (aT-cells), tumor-specific T-cells (T-cells), macrophages, monocytes, dendritic cells (DC)) in each of the indicated organs (tumor, liver, lung, lymph node (LN) and spleen) following transfer of each cell type to mice carrying intrahepatic LLC tumors and compared to mice not receiving cell transfer (No Transfer). Mice were sacrificed at 72 hours, organs were harvested and CD45.1+ cells were isolated via FACS.

VSV-MDSC Treatment Prolongs Survival and is Superior to Peripherally Injected VSV The foregoing Examples demonstrated that treatment with VSV-MDSC is safe and effective for shrinking the size of metastatic colon cancer tumors. The present Example demonstrates that VSV-MDSC treatment prolong survivals and that treatment with VSV-MDSCs is superior to injecting VSV peripherally. Mice with intrahepatic MCA26 tumors were treated with VSV-MDSCs (MOI: 300; n=9) and compared to PBS controls (p<0.0004; n=10) for survival. Mice receiving VSV-MDSCs lived significantly longer than mice receiving PBS injection alone (p<0.0004; n=10), MDSCs alone (p<0.002, n=3), the Ly6C$^-$ cell fraction (non-MDSCs), acquired during MDSC acquisition and infected with VSV at MOI: 300 (p<0.002, n=5), or an equivalent amount of free VSV-GFP virus (p<0.0001; n=10) (FIG. 6). To ensure that the observed effects can be attributed to the tumor targeting abilities of the MDSCs and the tumor lytic effects of VSV, mice were treated with MDSCs alone (n=6) and Ly6C$^-$ cells cultured with VSV (n=10). Again, VSV-MDSC treated mice lived longer than the other treatment groups (MDSC p<0.0002; Ly6C-p<0.002), whereas mice treated solely with MDSCs tended to die earlier than PBS controls, as would be expected.

It was also determined whether VSV-MDSCs were superior to a similar dose of peripherally injected rVSV-GFP. To determine the viral infective dose of VSV-MDSCs, first virally infected cells were lysed to obtain a TCID$_{50}$ using the Spearman-Karber method. From this it was determined that under optimal conditions, for every $5\times10^6$ VSV-MDSCs, at most, about $5\times10^7$ pfu VSV were being effectively delivered. When this dose was administered peripherally (n=10), however, it was determined to be significantly inferior to VSV-MDSC treatment (p<0.0001), and was no better than PBS controls (FIG. 6). Thus, MDSCs loaded with VSV were effective at prolonging survival in a metastatic tumor model, proving more effective than VSV administered alone.

To confirm the tumor-specific virus delivery of MDSCs, mice tumors and livers were harvested after treatment and stained for VSV-G antigen. Mice treated with VSV-MDSCs showed much stronger immunostaining than either controls, Ly6C$^-$ cells with VSV, or rVSV-GFP alone. In each of these groups, there was very little staining above the background in the liver, demonstrating the specificity of VSV for infecting tumor cells specifically, and not normal host cells. Some positivity was observed in the tumors treated with either the Ly6C$^-$ cells infected with VSV or with the rVSV-GFP alone, indicating that some of the injected virus reached the tumor site; however, the dose of VSV being delivered to the tumor site in these groups was not effective for treating the tumor.

Example 5

Optimization of Therapeutic Efficacy of VSV-MDSC Treatment

This Example demonstrated that direct conjugation of MDSCs to virus can increase the efficiency of viral loading of MDSCs, and that mutant viruses, with increased potency for treating tumors can be used in combination with MDSCs to treat tumors.

To further improve viral loading of MDSCs with VSV, a non-neutralizing monoclonal antibody directed against the G protein on the surface of VSV was utilized. Upon binding the virus, the antibody is then bound to Fc receptors present on the surface of MDSCs, thus increasing the binding efficacy between virus and cell approximately 80-fold. Another strategy for optimizing therapeutic efficacy of VSV-loaded MDSC is to alter the type of virus being targeted against the tumor cells. For example, rVSV(MΔ51)-M3 ("M3") is a second generation VSV virus which has been engineered to express the gammaherpesvirus protein M3 on its surface, leading to significantly decreased antiviral clearance by the host immune system [Wu et al, 2008, supra].

By employing these two strategies in tandem the efficacy of oncolytic virus conjugation to MDSCs for cancer treatment was even further optimized. While a survival benefit has been demonstrated for MDSCs passively loaded with VSV, VSV does not readily associate with MDSCs in significant numbers and, even under optimal conditions, it is difficult to conjugate more than one viral particle per cell, on average.

To enhance viral loading of MDSCs, a non-neutralizing monoclonal antibody directed against the VSV G-protein was tested to determine if it could increase the level of VSV binding, serving as a stable bridge between the virus and the Fc receptors present on MDSCs.

rVSV-GFP ($1.5\times10^{109}$) was bound to the optimal amount of antibody (15 μg), polybrene (10 microg/ml) in 500 ml and then mixed with 5x10e6 MDSCs. MDSCs loaded with antibody-bound virus demonstrated greater than a 30-fold increase in VSV staining (FIG. 7A) and GFP expression (FIG. 8) over VSV-MDSCs generated by passive coupling at various MOIs ($6.95\times10^4$ viral particles for MOI: 30 with antibody vs. $5.72\times10^4$ viral particles at MOI: 1000 without antibody, p=0.003; FIG. 7A). $TCID_{50}$ assays were then performed on BHK-21 cells using VSV-MDSCs generated with and without antibody at a virus to MDSC ratio of 300. A 70-fold increase in viral titer was observed when comparing antibody-conjugated VSV-MDSCs versus passively-coupled VSV-MDSCs ($3.9\times10^7\pm1.1\times10^7$ vs $5.6\times10^5\pm8.6\times10^4$ $TCID_{50}$ per $5\times10^6$ cells, p<0.01; FIG. 7B).

Another strategy for improving therapeutic efficacy is to increase the oncolytic potential of the virus in a manner that will not worsen the safety profile. rVSV(MΔ51)-M3 (VSV (M3)) is a second generation VSV engineered with an altered viral matrix protein which improves the safety profile of rVSV by attenuating its ability to inhibit cellular protein synthesis and, thus, rendering the virus more susceptible to the interferon response of normal cells. To combat the robust host antiviral immune response, which limits viral replication in the tumor, this recombinant VSV has been engineered to express the murine gammaherpesvirus M3 protein, which binds a variety of chemokines with high affinity, leading to a significant decrease in antiviral clearance [Wu, 2008, supra].

We next tested these two strategies in tandem, treating BALB/c mice bearing hepatic MCA26 liver tumors with MDSCs conjugated to VSV(M3) via Fc receptor-bound antibody against VSV-G protein (MDSC+Ab+VSV(M3)). MDSC+Ab+VSV(M3) treatment led to long-term survival in 4 of 15 (26.3%) mice. The median survival in these mice was significantly increased compared to the PBS controls (n=15, 52.9 days vs. 24.6 days p<0.0001; FIG. 7C) as well as compared to mice treated with Ly6C− cells+antibody-conjugated to VSV(M3) (n=15, median survival=24.0 days, p<0.0001; FIG. 7C). The median survival of MDSC+Ab+VSV(M3) mice was also significantly longer than in mice treated systemically with VSV(M3) (n=15, median survival=24.9 days p<0.0001; FIG. 7C). Similarly, mice treated with MDSC+Ab+VSV(M3) outlived mice treated with MDSCs conjugated to rVSV-GFP virus (MDSC+Ab+VSV(GFP); n=15, median survival=29.8 days, p=0.0009; FIG. 7C) indicating that the survival benefit is from the combined effect of the improved viral vector and antibody-mediated improvement of viral load on MDSC, and that the key element in providing a survival benefit is MDSC-mediated tumor targeting.

Example 6

MDSCs are Strongly Tumor-Trophic

This Example demonstrates that MDSCs are more strongly tumor-trophic than other immune cells tested.

To determine which subset of immune cells possess the strongest tumor tropism, a series of experiments were performed in which CD45.1+ MDSCs, CIKs (cytokine induced killer cells), tumor-specific T-cells, activated T-cells, monocytes, macrophages, and dendritic cells were adoptively transferred into CD45.2+ mice carrying LLC hepatic tumors, simulating metastatic lung cancer (FIG. 8). After 72 hours, mice were sacrificed and CD45.1 cells were identified in various organs. Significant homing of MDSCs to tumor-sites compared to spleen and liver was observed ($1.28\times10^5\pm2.15\times10^4$ cells vs $3.78\times10^4\pm1.17\times10^4$ (p=0.03) vs $1.04\times10^4\pm6.71\times10^3$ (p=0.0003)). MDSCs also demonstrated stronger tumor tropism than CIKs ($6.45\times10^3\pm4.12\times10^3$, p=0.001), tumor-specific T-cells (603±244, p=0.0008), activated T-cells ($1.13\times10^3\pm350$, p=0.0009), monocytes ($5.32\times10^3\pm1.23\times10^3$, p=0.001), macrophages (546±197, p=0.0008), and dendritic cells (666±239, p=0.005) indicating that MDSCs had greater potential in the delivery of tumor-specific therapies than all of the other cell types analyzed (FIG. 9).

Example 7

Confirmation of Tumor-Specific Delivery of VSV-MDSCs

This Example demonstrates that MDSC-mediated delivery of VSV exhibits greater tumor-specificity than systemic treatment with free virus.

Representative mice from each treatment group were sacrificed at 96 hours post-treatment and their tumors and organs were harvested. Staining for VSV-G was performed. Tumors from mice treated with various MDSC-mediated therapies MDSC+Ab+VSV(M3), MDSC+Ab+VSV(GFP), and VSV-MDSCs (passively infected with VSV(M3), but without antibody) demonstrated stronger staining than tumors from controls or animals treated with free virus. On the other hand, intense staining was observed in the spleens and lungs, and to a lesser degree in the liver, from mice treated with free VSV (M3), and not in the mice treated with MDSC-targeted therapy, indicating that free virus lacks the tumor-targeting specificity of MDSC-mediated therapies. Brains from these mice were also examined for VSV-G staining as a surrogate sign of potential neuropathic effects known to complicate VSV therapy. Free VSV treatment resulted in some brain positivity, which was not observed in the MDSC-targeted VSV groups, indicating that MDSC-targeted therapy is also safer than free virus therapy, likely due to the blood brain barrier preventing cell migration as well as the tumor-specific tropism of MDSCs. Pathologic examination of the brains and spinal cords of mice in which long-term survival had been achieved with MDSC+Ab+VSV(M3) treatment, revealed no abnormalities or pathological changes. Specifically, no abnormalities were noted among the myelination of central or peripheral nervous system tissue, neuron density, or morphology of the cerebral cortex or purkinje cell concentration within the cerebellum. In addition, there were no signs of ischemic damage or tissue necrosis. Necrosis was observed within the tumors of mice treated with MDSC+Ab+VSV (M3) but not the other MDSC-targeted virus therapies at this time point, indicating that this method of delivery not only targets the tumor specifically but also promotes more efficient oncolytic viral replication.

To confirm these findings, organs from mice receiving free VSV(M3), VSV-MDSCs, and MDSC+Ab+VSV(M3) were harvested and $TCID_{50}$ experiments were performed. Tumors of mice that received VSV-MDSCs or MDSC+Ab+VSV(M3) had significantly more virus than those of mice that received free VSV(M3) (26.2±1.6 $TCID_{50}$/organ vs 44.3±7.0 vs 16.5±1.2; p=0.03). Mice receiving MDSC+Ab+VSV(M3) also demonstrated significantly more virus in the tumor than in spleen (2.4±0.25; p=0.05), liver (3.7±1.6, p=0.03), lungs (3.2±0.89, p=0.02), and brain (2.0±0.43, p=0.02). Interestingly, brains of mice treated with VSV-MDSCs and MDSC+Ab+VSV(M3) also demonstrated significantly less virus than those receiving VSV(M3) (3.2±0.050 vs 2.0±0.43 vs 4.7±0.63; p=0.03 and p=0.01) (FIG. 10A).

Further confirmation was demonstrated through qPCR of cell lysates from the organs of mice treated with free VSV (M3), VSV-MDSCs, and MDSC+Ab+VSV(M3) (FIG. 10B). Again, tumors in mice receiving VSV-MDSCs and MDSC+Ab+VSV(M3) demonstrated significantly more viral RNA than those receiving free VSV(M3) (23.4±3.6 copy #/g tissue vs 37.3±7.4 vs 5.9±1.7; p=0.008 and p=0.05). Mice that received MDSC+Ab+VSV(M3) also demonstrated significantly more viral RNA in the tumor than in spleen (7.0±2.3; p=0.03), liver (15.6±1.6, p=0.05), lungs (10.8±4.6, p=0.05), and brain (5.5±2.6, p=0.05) (FIG. 10B).

Example 8

MDSCs Exposed to VSV(M3) Demonstrate an M1-Like Phenotype

The Example demonstrates that MDCS exposed to VSV (M3) demonstrate an M1-like phenotype.

Figure 11A:
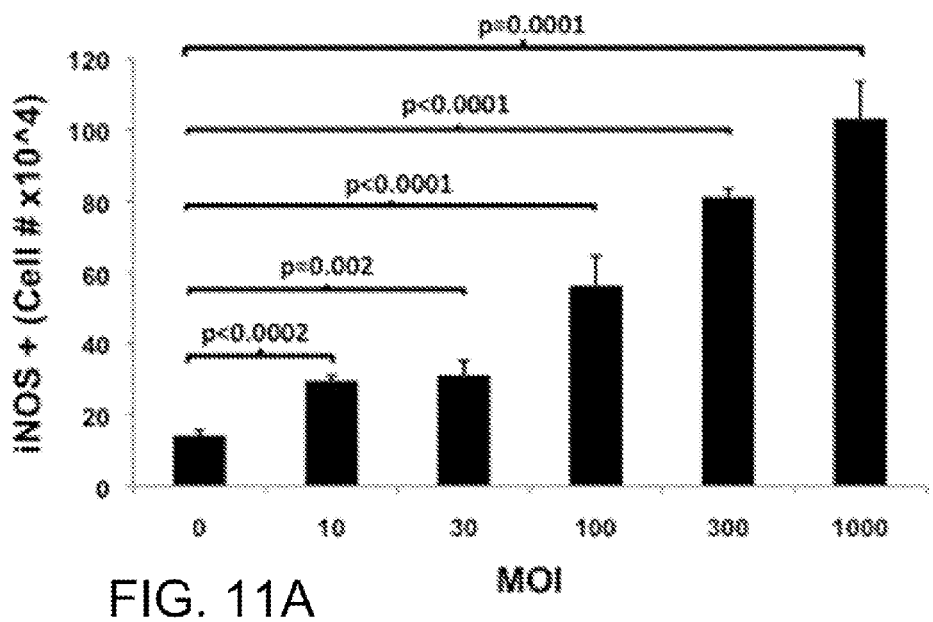
FIG. 11A and FIG. 11B are graphs quantifying the number of iNOS (11A) or Arg (11B) positive cells×10^4 at the indicated MOI in MDSC+anti-VSV-G antibody (Ab)+VSV(M3) subjected to intracellular staining for iNOS and Arg.
Figure 11B:
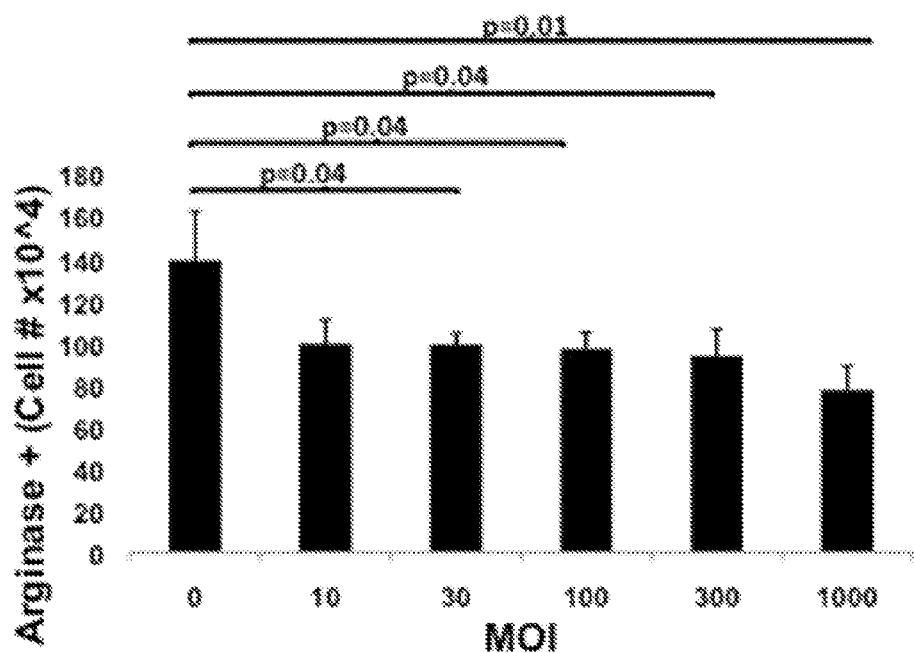

Since MDSCs have been shown to promote an M2-like, pro-tumor environment, it may be counterintuitive to use this cell type to kill tumors. However, the M2 like phenotype is plastic and, under certain conditions, can exhibit M1-like characteristics. To determine whether MDSCs exposed to VSV(M3) shifted to the M1 phenotype, MDSCs were analyzed for expression of the M1 marker, inducible nitric oxide synthase (iNOS), and the M2 marker, arginase (Arg), at various MOIs of VSV infection. The number of cells staining positive for iNOS after culture with VSV(M3) increased with the amount of virus from $1.4 \times 10^4 \pm 1.3 \times 10^3$ iNOS+ cells without any virus, to $3.0 \times 10^4 \pm 1.4 \times 10^3$ iNOS+ cells at an MOI of 10 (p<0.0002) up to $1.0 \times 10^5 \pm 1.0 \times 10^4$ iNOS+ cells at an MOI of 1000 (p=0.0001) (FIG. 11A). At the same time, after culture with VSV(M3), Arg+ cells decreased, from $1.3 \times 10^5 \pm 2.3 \times 10^4$ Arg+ cells without any virus to $9.9 \times 10^4 \pm 5.2 \times 10^3$ Arg+ cells at an MOI of 10 (p=0.04), down to $7.7 \times 10^4 \pm 1.1 \times 10^4$ Arg+ cells at an MOI of 1000 (p=0.01) (FIG. 11B).

Figure 11C:
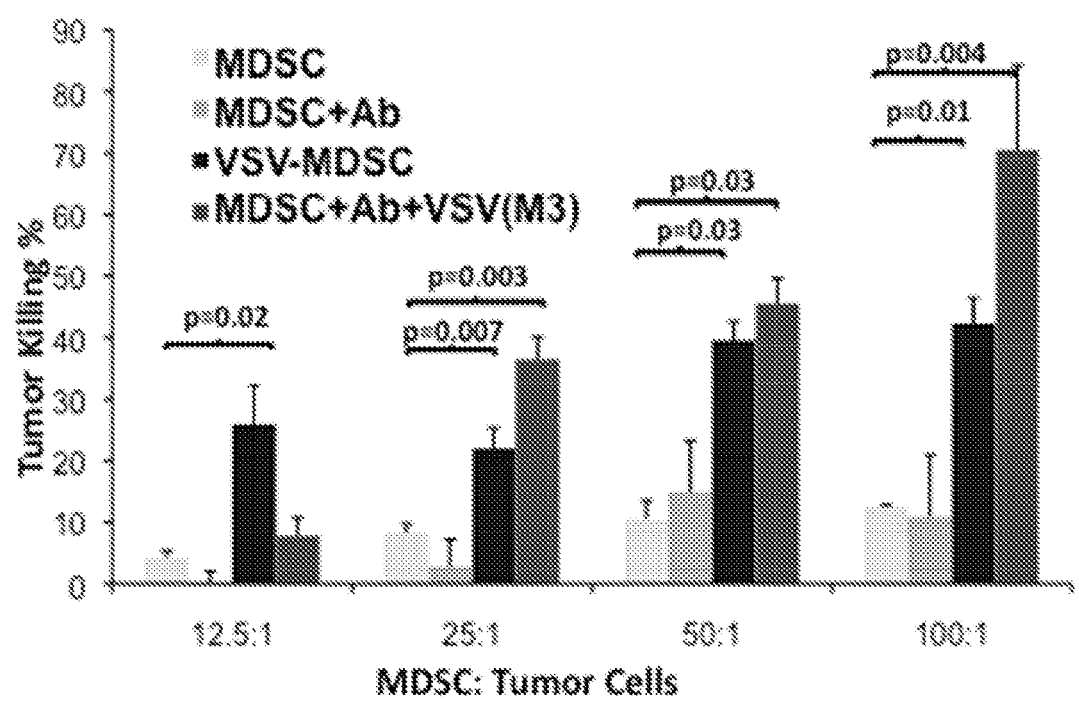
FIG. 11C is a bar graph showing the percent tumor killing after 4 hours in cocultures of LLC tumor cells and MDSC+Ab+VSV (M3), VSV-MDSC, MDSC+Ab, or MDSC in a ratio of 12.5: 1, 25:1, 50:1, or 100:1 (MDSC:tumor cells). Cell killing was measured as LDH release. Statistical significance (p value) is indicated.

To further demonstrate that MDSCs exposed to VSV(M3) demonstrated an M1-like phenotype, a cell lysis assay was performed in the presence of tumor cells comparing MDSCs to MDSCs cocultured with the VSV-G antibody (Ab) alone (MDSC+Ab), VSV-MDSCs, and MDSC+Ab+VSV(M3) (FIG. 11C). After 48 hours of culture of infected MDSC, tumor killing (lysis) was assayed by measuring release of lactate dehydrogenase (LDH) in the presence MDSC for four hours. Any tumor cell lysis observed was directly attributable to MDSC-mediated cell killing, since the tumor cells were only exposed to the virus for 4 hours and it takes 48-72 hours for virus to induce cell lysis. Significantly increased tumor killing at all ratios of MDSC: tumor cells was observed in the groups where MDSCs had been exposed to virus, compared to MDSCs not exposed to virus (FIG. 11C). Upregulation of iNOS in MDSCs exposed to both antibody and virus and downregulation of Arg was also observed. Thus, MDSCs, when exposed to virus and antibody, demonstrated an M1-like phenotype, including upregulating iNOS, downregulating Arg, and killing tumor cells.

Example 9

MDSC Mediate Nanoparticle Delivery to Metastatic Tumor Sites as Direct Antigen Presenting Cells This Example shows that MDSCs loaded with antigen-conjugated nanoparticles are more effective for delivering nanoparticles to tumor metastatic target sites compared to systemic delivery or subcutaneous injection.

Figure 12B:
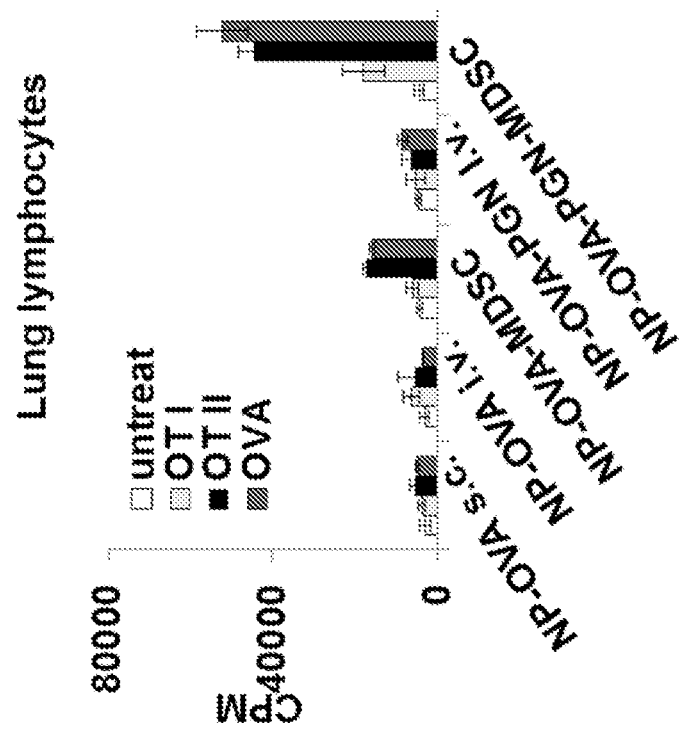
FIG. 12A and FIG. 12B are bar graphs showing in vitro proliferation (expressed as counts per minute (CPM)) in response to OTI, OTII and OVA peptides by assay of Thy1.2 T cells (FIG. 12A) and lung lymphocytes (FIG. 12B) isolated from mice i.v. challenged with 3×10^5 OVA-B16 melanoma cells for 7 days and then vaccinated with NP-OVA+/−PGN with indicated delivery (s.c.—subcutaneous, i.v.—intravenous, or by MDSC).
Figure 12A:
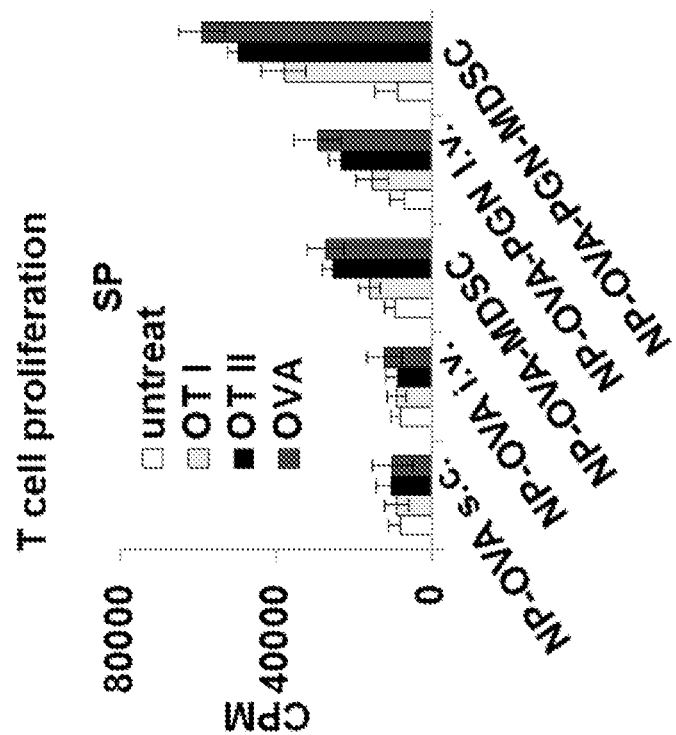
Figure 13:
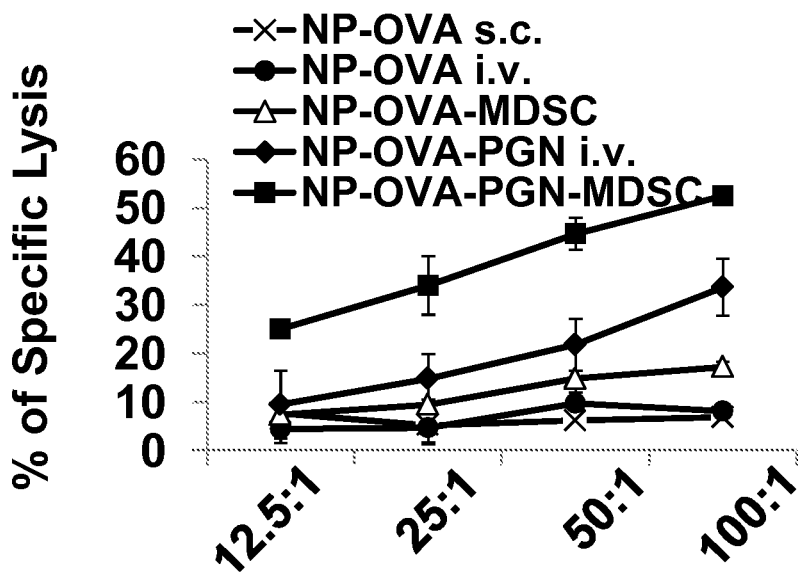
FIG. 13 is a graph showing the cytotoxic T lymphocyte (CTL) activity of purified Thy1.2 T cell in spleens of vaccinated mice, expressed as percent (%) of specific lysis, in the same groups as in FIGS. 12A, 12B FIG. 14 contains graphs quantifying the percentage of T regulatory cells ("Treg") in mice that were intrahepatically inoculated with 4×10^7 OVA-B16 melanoma cells for 10 days and vaccinated with NP-OVA+/−PGN with indicated delivery (i.v.—intravenous or via MDSCs) and sunitinib malate. Sunitinib malate ("su") was given daily at the dose of 0.015 mg/mice/day. After 10 days, the expression of CD25 and FoxP3 of OT-II-specific T cells in tumor tissues were analyzed by gating on CD4+CD45.1+ T cells. The bars represent the percentage of CD25+FoxP3+ T cells (left) and IL-17 (middle) and IFNγ (right) production of CD4+CD45.1+ T cells in spleen, analyzed after re-stimulated with OTII antigens.

To determine which delivery strategy can induce effective immune response in the tumor microenvironment, different strategies to deliver nanoparticle conjugated with OVA with or without the TLR ligand peptidoglycan (PGN) were tested in B16-OVA melanoma metastasis model, including intravenously and subcutaneously systemic injection or loading with MDSC. OVA+/−PGN conjugated nanoparticle (NP-OVA and NP-OVA-PGN), delivered by systemic injection or by MDSC, significantly increased T cell proliferation in spleen in response to OTI, OTH or OVA (FIG. 12A). Interestingly, only when NP-OVA or NP-OVA-PGN was loaded in MDSC was leukocytes proliferation enhanced in the target metastasis site (lung) in response to OTI, OTH or OVA (FIG. 12B). Furthermore, vaccination with NP-OVA-PGN-loaded MDSC elicited the highest cytotoxic T cell activity in spleen on B16-OVA cells (FIG. 13).

Figure 14:
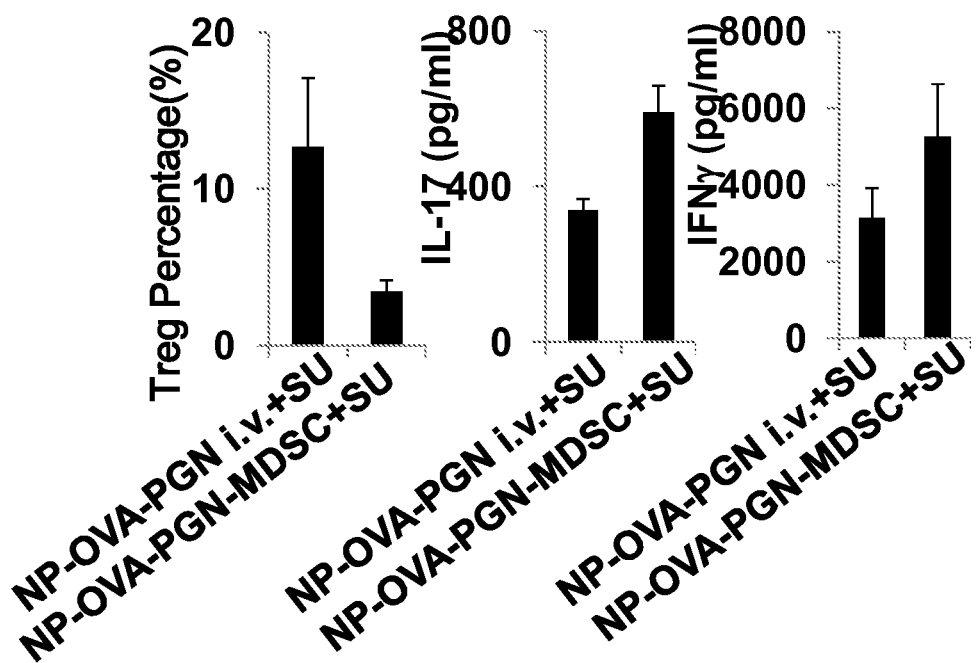

The therapeutic effects of NP-OVA-PGN delivered either systemically (intravenous injection) or using MDSCs and combined with sunitinib malate treatment were compared in intrahepatic melanoma cells. B16-OVA cells were inoculated intrahepatically in syngeneic C57BL/6 mice ($7 \times 10^4$ B16-OVA cells/mouse). All mice received adoptively transferred OTII-TCR T cells with CD45.1 congenic markers ($5 \times 10^6$/mouse) and continuous sunitinib malate treatment (0.015 mg/mice/day). It was observed that NP-OVA-PGN-loaded MDSC effectively decreased the percentage of OTII-specific Treg cells (CD25+Foxp3+ cells) in the tumor site compared to systemic administration (4.73% v. 15.1%, respectively), and increased IL-17 and IFNγ production from OTII-specific T cells purified from spleen (FIG. 14). These results demonstrated that MDSCs are ideal carriers of nanoparticles to deliver antigenic as well as TLR signals specifically to tumor sites and are more effective than systemic deliver of nanoparticles.

Example 10

Nanoparticle-OVA-PGN-Loaded MDSCs in a Hepatic Metastatic Melanoma Model

This Example demonstrates that MDSCs loaded with nanoparticles conjugated to PGN and OVA and administered to mice in an intrahepatic metastatic OVA-B 16 melanoma model with sunitinib malate have a therapeutic effect.

Figure 15:
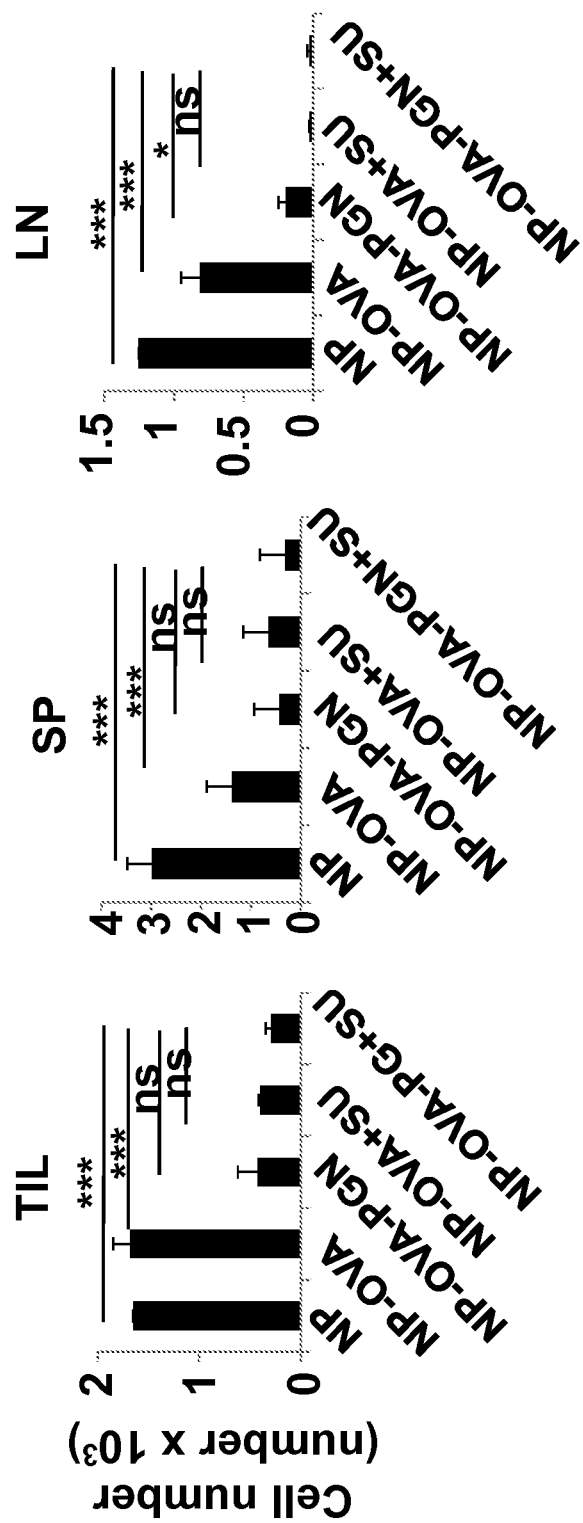
FIG. 15 shows graphs showing the mean and standard deviation of cell number of CD4+CD25+ Foxp3+ T regulatory cells in the TIL cells or in the spleen (SP) or lymph nodes (LN) in the indicated groups. Purified MDSCs were pulsed with control nanoparticle (NP), nanoparticle conjugated with OVA (NP-OVA), or nanoparticle conjugated with OVA and PGN (NP-OVA-PGN) for 12 hours. The indicated nanoparticles-loaded MDSCs and CD45.1+CD4+ OTII-specific TCR T cells (5×10^6 cells/mice) were co-adoptively transferred into OVA-B16-intrahepatic tumor bearing mice. Sunitinib malate was given 0.015 mg/day continuously for 10 days. After 10 days, the phenotypic changes of OT-II-specific T cells in tumor tissues, lymph nodes, and spleens were assayed. (A) The development of OT-II-specific Treg in different organs of test tumor bearing mice. **p=0.05; "ns" means not statistically significant.
Figure 16:
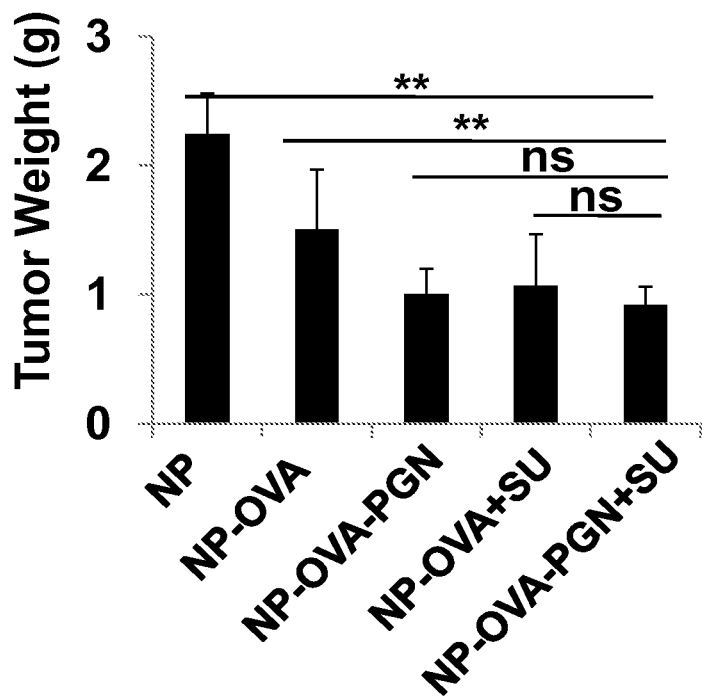
FIG. 16 is a graph showing the tumor size after 10 days of the indicated treatments described above for FIG. 15.

To evaluate the therapeutic effect of NP-OVA-PGN-loaded MDSCs on intrahepatic melanoma, B16-OVA cells were inoculated intrahepatically in syngeneic C57BL/6 mice ($7 \times 10^4$ B16-OVA cells/mouse). When tumors reached the size of $3 \times 3 \times 3$ mm$^2$, tumor-bearing mice were divided randomly into 5 groups: NP (empty nanoparticle carrier); nanoparticle conjugated with OVA (NP-OVA); combination of NP-OVA-loaded MDSC and sunitinib malate treatment (NP-OVA+SU); nanoparticle conjugated with OVA and PGN (NP-OVA-PGN); combination of NP-OVA-PGN-loaded MDSC and sunitinib malate treatment (NP-OVA-PGN+SU) (n=2~5/group). All mice received adoptively transferred OTII-TCR T cells with CD45.1 congenic markers ($5 \times 10^6$/mouse) and indicated MDSCs ($5 \times 10^6$/mouse). Sunitinib malate treatment was continuously given (0.015 mg/mice/day). After adoptive transfer for 10 days, mice were sacrificed and CD45.1+ T cells were purified from spleen for T cell proliferation and cytokine production assay. The phenotypic changes of adoptively transferred CD45.1+OTII-TCR T cells in the spleen, lymph node and tumor were detected by gating on CD4+ CD45.1+ cells. FoxP3+CD25+ Tregs were significantly decreased in tumor tissue of mice in NP-OVA-PGN (7.54%), NP-OVA+SU (16.6%), NP-OVA-PGN+SU (5.17%) groups, when compared to NP group (76.6%) (FIG. 15). The results obtained from spleen and lymph nodes were similar to that obtained from tumor tissue. It was observed that NP-OVA-PGN-loaded MDSC with (NP-OVA-PGN+SU) or without (NP-OVA-PGN) sunitinib malate treatment dramatically decreased tumor growth (FIG. 16).

Figure 17:
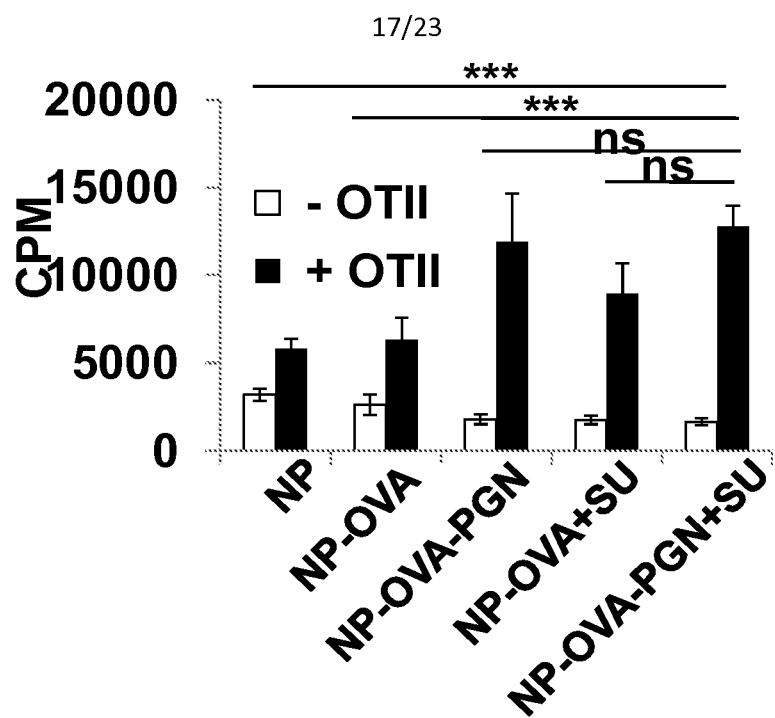
FIG. 17 is a graph quantifying T cell proliferation. The CD45.1+OT-II-specific T cells were recovered from the groups indicated and described above for FIG. 15 and purified for T cell proliferation assay in response to OT-II peptides; ***p=0.01; "ns" means not statistically significant. Black bar with OT-II peptide, white bar without OT-II peptide.
Figure 18:
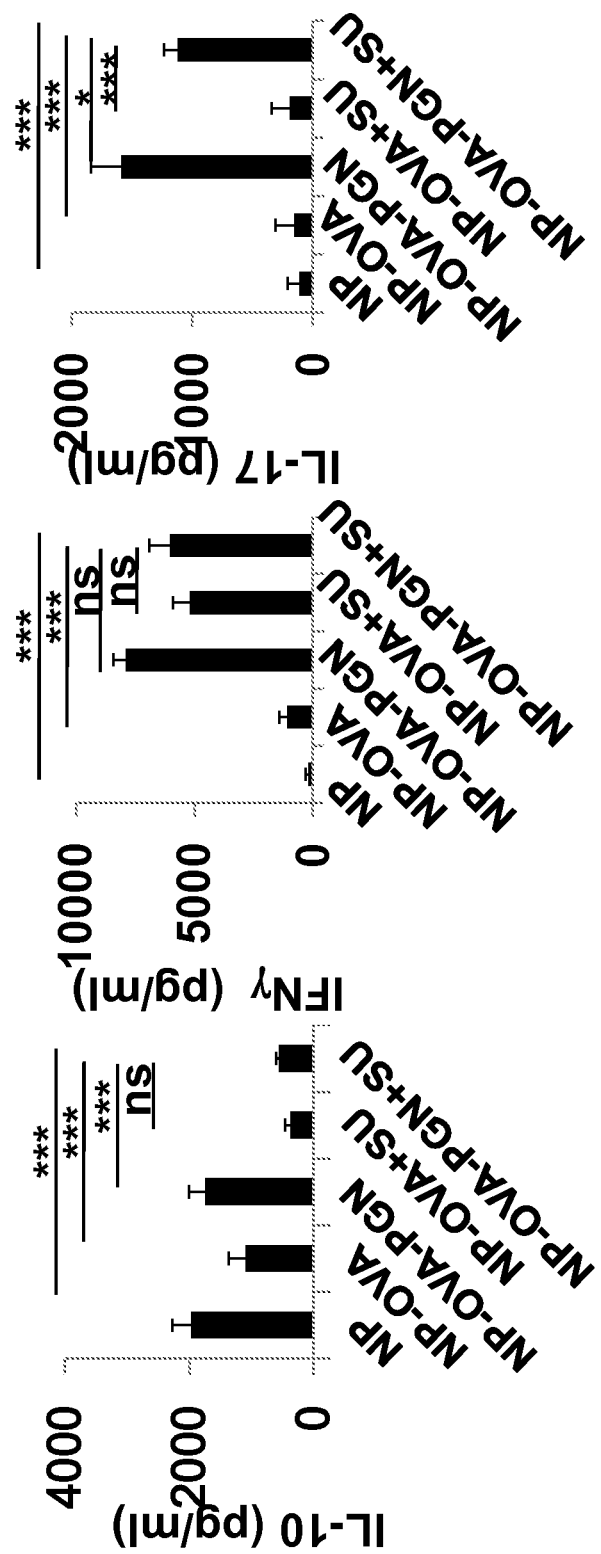
FIG. 18 contains graphs quantifying IL-17, IL-10 and IFNγ production in the culture supernatant from CD45.1+OT-II-specific T cells collected from the groups indicated and described above. ***p=0.01; "ns" means not statistically significant.

As expected, CD45.1+OTII-TCR T cells purified from these two groups (NP-OVA-PGN+SU and NP-OVA-PGN) showed significant levels of T cell proliferation in response to OTII peptides compared to negative control (without OTII peptide) (FIG. 17). Less T cell proliferation was observed in mice treated with NP-OVA-loaded MDSCs with (NP-OVA+SU) or without (NP-OVA) sunitinib malate treatment (FIG. 17). High levels of IFNγ and IL-17 and low levels of IL-10 were detected in CD45.1+OTII-TCR T cells from mice in NP-OVA-PGN and NP-OVA-PGN+SU group (FIG. 18). On the other hand, the combination of NP-OVA-PGN+SU treatment synergistically decreased IL-10 expression. These results indicated that adoptive transfer of NP-OVA-PGN-loaded MDSC and sunitinib malate treatment can effectively control B16-OVA tumor through different mechanisms. Loading MDSC with NP-OVA with PGN conjugation significantly decreased Treg (from 63.8% to 7.54%), increased IFNγ and IL-17 production (7.3 fold and 10.3 fold of NP-OVA group, respectively), reduce tumor size (66% of NP-OVA group) and augment antigen-specific T cells proliferation (FIG. 18). Thus, sunitinib malate does not only act as an immune-modulator to convert Treg to Th1/Th17, enhance antigen-specific T cells proliferation, direct MDSC differentiation into M1 macrophage, thereby switching the tolerogenic microenvironment to a pro-inflammatory microenvironment; sunitinib malate can also act as a chemotherapeutic drug against tumor cells.

Example 11

Nanoparticle-OVA-PGN-Loaded MDSCs in Lung Metastatic Melanoma Model

This Example demonstrates that MDSCs loaded with nanoparticles conjugated to PGN and OVA and administered to mice in a lung metastatic melanoma model have a therapeutic effect.

Figure 19:
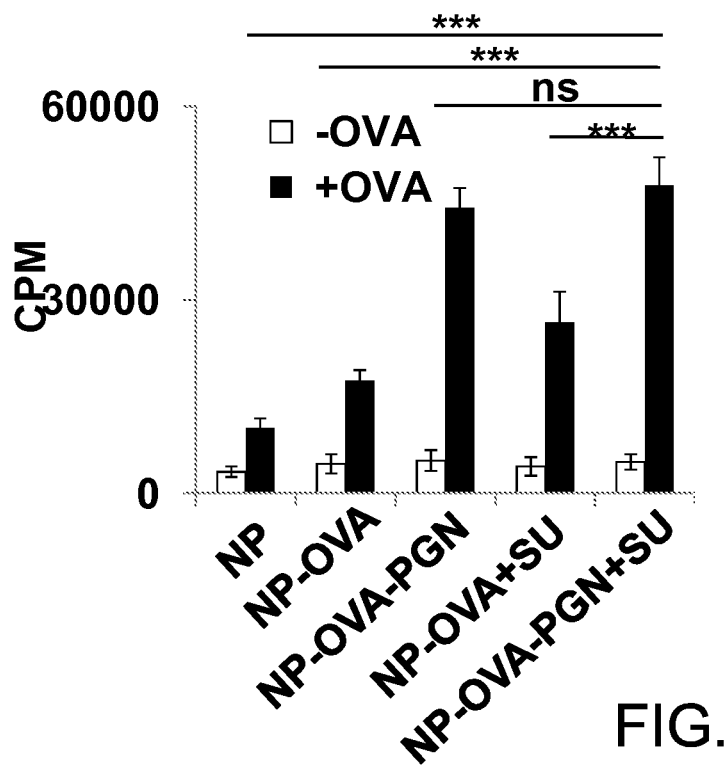
FIG. 19 is a graph quantifying proliferation of Thy1.2 T cells purified from spleens of vaccinated mice after MDSC adoptive transfer in response to OVA proteins (+OVA) and in the presence of antigen presenting cells. The mice were injected i.v. with OVA-B16 melanoma cells. Mice bearing OVA-B16 tumors were divided into the following treatment groups: NP (control nanoparticle carrier); nanoparticle conjugated with OVA (NP-OVA); combination of NP-OVA-loaded MDSC and sunitinib malate treatment (NP-OVA+ SU); nanoparticle conjugated with OVA and PGN (NP-OVA-PGN); combination of NP-OVA-PGN-loaded MDSC and sutent treatment (NP-OVA-PGN+SU). 10 mice per group. After 7 days, the indicated nanoparticles-loaded MDSCs were adoptively transferred into test mice. Sunitinib malate treatment was continuously injected for 28 days (0.015 mg/mice/day). ***p=0.01; "ns" means not statistically significant. No OVA (−OVA) was used as a control in the in vitro proliferation assay.
Figure 20:
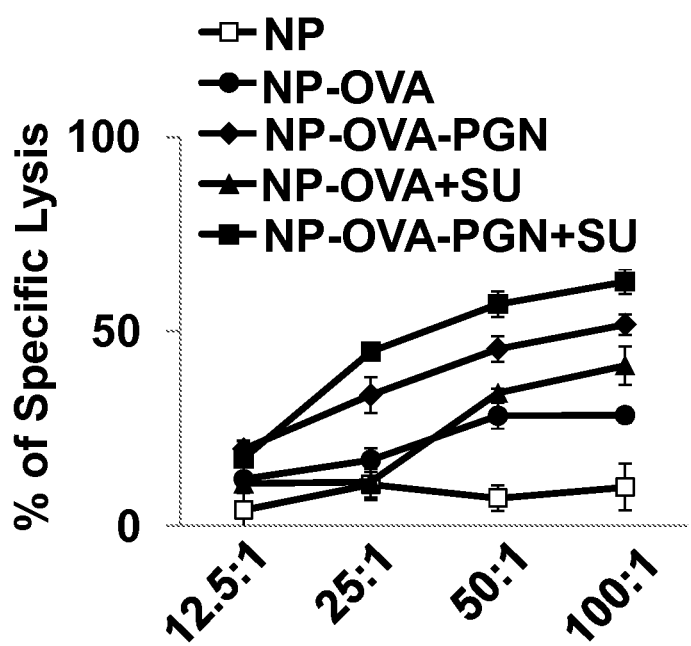
FIG. 20 is a line graph quantifying cytotoxic T lymphocyte activity on OVA-B16 tumor cells (expressed as percent (%) lysis of the T cells isolated from the groups described above for FIG. 19. The x-axis indicates the ratio of T cell to tumor cell.

An animal lung metastatic model was used to assess the therapeutic effect of the combination of MDSCs and sunitinib malate therapy. Mice were intravenously challenged with B16-OVA cells ($3 \times 10^5$ cells/mouse) 7 days before adoptive transfer of nanoparticle-loaded MDSCs ($5 \times 10^6$ cells/mouse). Sunitinib malate treatment was continuously injected for 28 days (0.015 mg/mice/day). To assess whether the combination therapy of PGN and sunitinib malate can increase specific T cell proliferation and induce cytotoxic T lymphocyte activity against B16-OVA melanoma cells, Thy1.2 T cells were purified from spleen of mice in all groups on day 14 after MDSC adoptive transfer. PGN conjugation with NP-OVA substantially increased OVA-specific T cell proliferation, both with and without sunitinib malate treatment (stimulation index: 9.82 and 8.73, respectively) (FIG. 19). To determine cytotoxic T lymphocyte (CTL) activity, purified Thy1.2 T cells were further in vitro re-stimulated with OVA for 3 days, and used as effector cells. IFNγ-pretreated B 16-OVA tumor cell were used as target cells. The combination of NP-OVA-PGN-loaded MDSCs and sunitinib malate elicited the highest CTL activity (FIG. 20). Significant but lower CTL activity was detected in the mice treated with NP-OVA-PGN-loaded MDSCs alone, or NP-OVA-loaded MDSCs plus sunitinib malate (FIG. 20).

Figure 21:
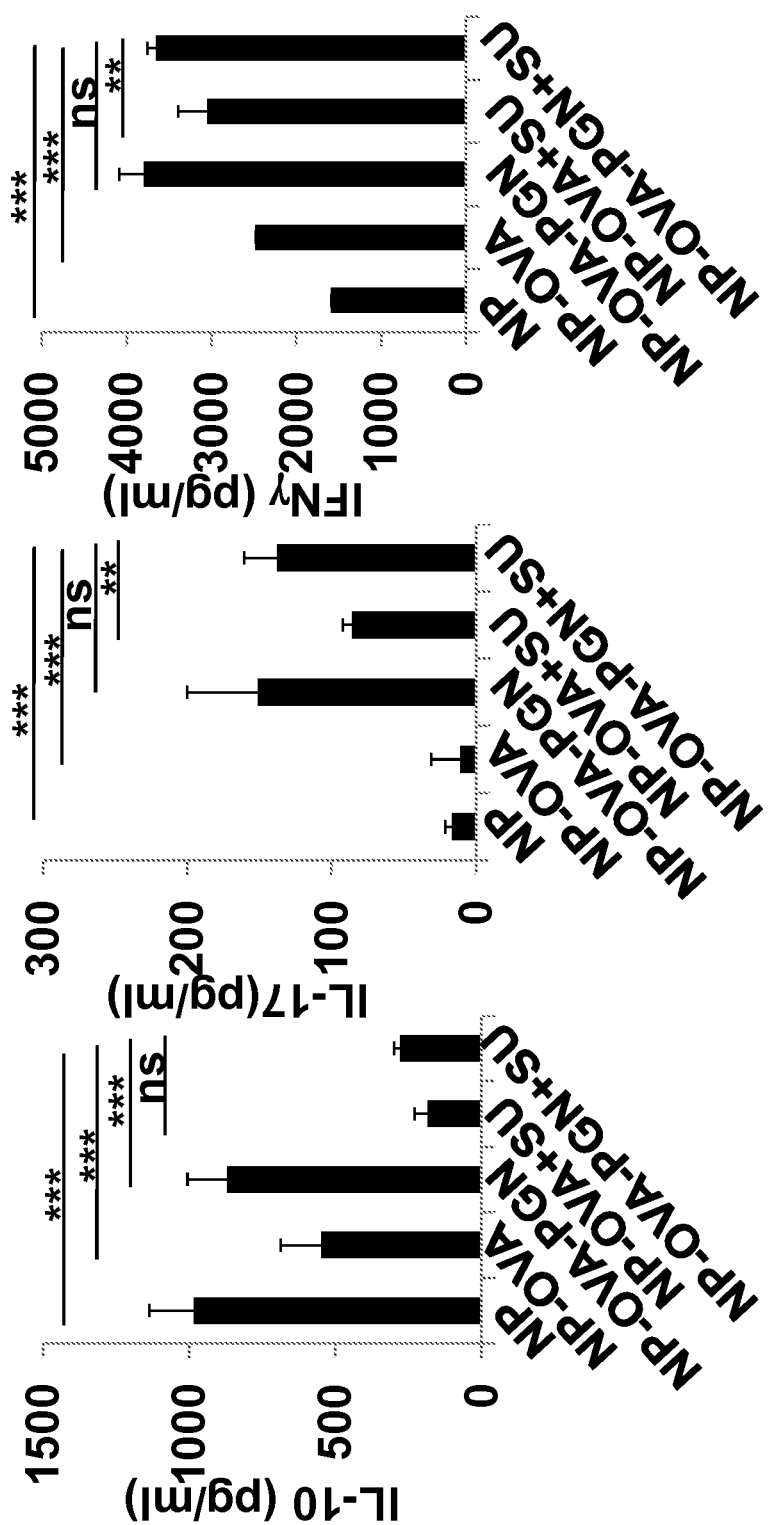
FIG. 21 contains bar graphs showing IL-10, IFNγ and IL-17 levels in the culture supernatants of restimulated Thy1.2 cells isolated as described for FIG. 19. *p=0.01; p=0.05; "ns" means not statistically significant.
Figure 22:
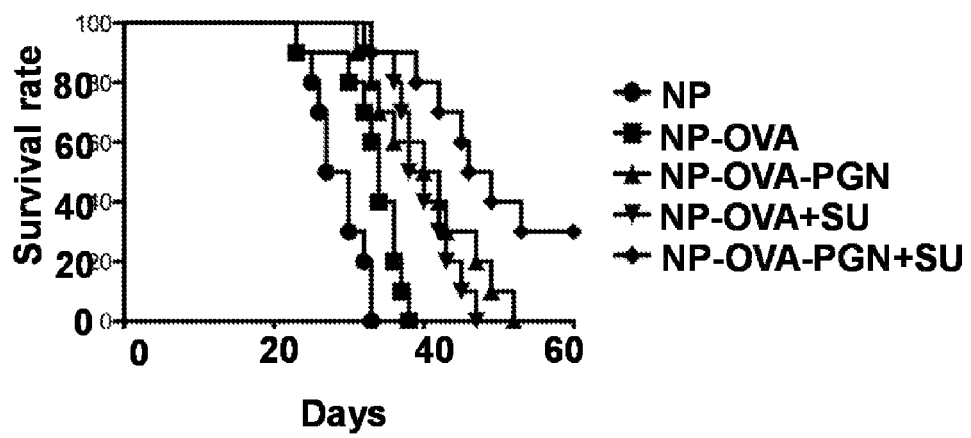
FIG. 22 is a Kaplan-Meier survival curve showing survival rates of test mice treated with indicated treatments. n=10 mice per group. The results are combined from two reproducible experiments. The treatment groups are as described for FIG. 19, above.
Figure 23:
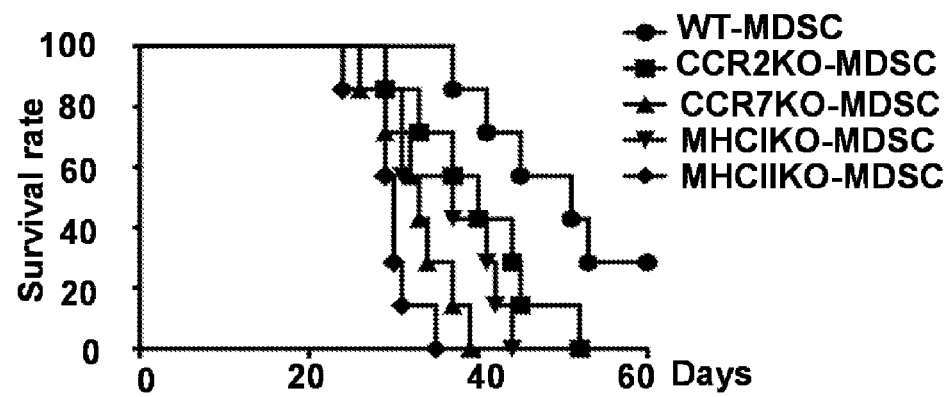
FIG. 23 is a Kaplan-Meier survival curve showing survival rates with MDSCs isolated from wild-type (WT), CCR2 knock out (KO), CCR7 KO, MHC class I KO and MHC class II KO tumor bearing mice and loaded with NP-OVA-PGN+ SU treatment for preexisting OVA-B16 lung metastases tumor model. These results indicate that MDSCs need to migrate to the tumor site to mediate their effect and can act as direct antigen presenting cells for T cell activation.

To evaluate cytokine profile of specific effector T cells in the target metastasis site, the total lymphocytes in metastatic lung tissue were isolated and re-stimulated with OVA for 3 days. Afterward, the supernatants from purified Thy1.2 T cells and isolated lung lymphocytes were collected for analysis of IFNγ and IL-17 production. The results showed that NP-OVA-PGN-loaded MDSC and/or sunitinib malate substantially and significantly enhanced IFNγ and IL-17 production, but decreased IL-10 production in spleen (FIG. 21). NP-OVA-PGN-loaded MDSC alone had the strongest effect on augmenting IL-17 production in the spleen (FIG. 21). On the other hand, sunitinib malate treatment significantly increased IFNγ production in metastatic lung lymphocytes. The long-term survival rate of test mice was traced (FIG. 22). The mice treated with NP-OVA-PGN-loaded MDSC+sunitinib malate showed significantly higher prolonged survival curve than the mice treated with NP-OVA-PGN-loaded MDSC (P=0.0378) or NP-OVA-loaded MDSC+sunitinib malate (P=0.0074). PGN conjugation with NP-OVA significantly improved the survival of treated mice (P=0.0092), when compared to the NP-OVA group. Thus, PGN may enhance immune responses against tumor by increasing antigen-specific T cell proliferation and CTL activity and promoting both Th1 and Th17 cells, especially Th17 cells. On the contrary, sunitinib malate likely exerts its anti-tumor effect through switching MDSC to specific M1 phenotypes and increasing IFNγ production in metastatic organs and spleen. With the combination of PGN and sunitinib malate, the promising therapeutic effects were obtained from significantly decreased Treg activation, increases Th1 and Th17 responses, retarded tumor growth and prolonged survival rate. The combination of PGN and sunitinib malate thus provides a strong basis to arm both chemotherapy and immunotherapy. Most importantly, the MDSC isolated from MHC class II, I or chemokine receptor KO mice (CCR2, CCR7) significantly impaired the survival benefit, indicating that the MDSCs needed to migrate to the tumor site and act as antigen presenting cells to the tumor specific T cells (FIG. 23).

Example 12

MDSC Mediated Nanoparticle Delivery in Metastatic Cervical Carcinoma Model

This Example demonstrates that MDSCs effectively deliver nanoparticles conjugated to tumor antigen to tumor sites and increase survival of tumor bearing mice in a metastatic cervical carcinoma model.

Figure 24:
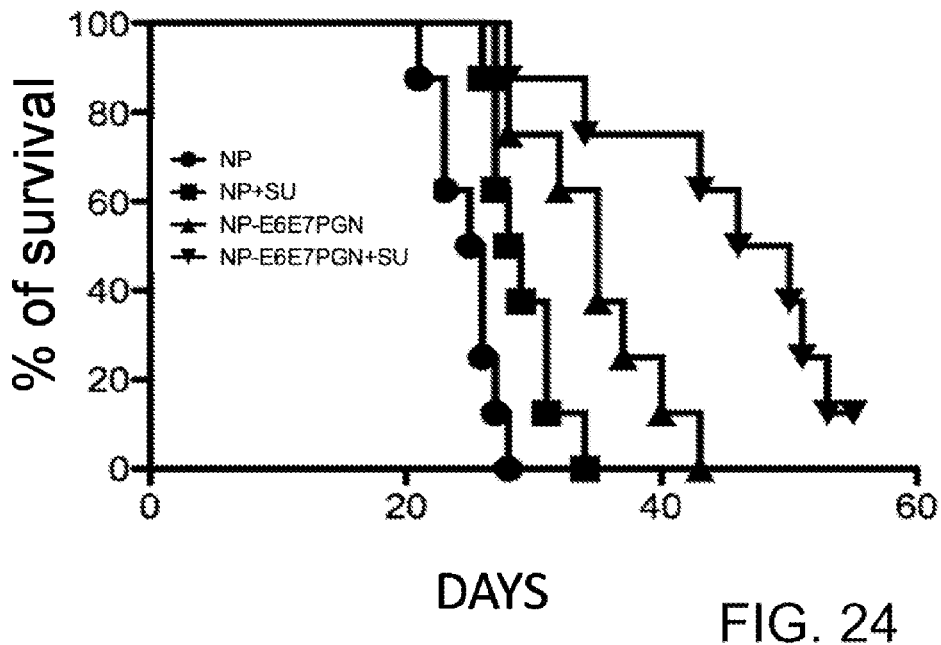
FIG. 24 is a Kaplan-Meier survival curve showing survival rates in test mice treated with indicated treatments. n=8 mice per group, Log rank analysis for the p value. Mice bearing TC-1 (cervical carcinoma with E6/E7 expression) lung metastases were injected i.v. with MDSCs loaded with nanoparticle alone (NP), with MDSCs loaded with NP and additionally treated with sunitinib malate (NP+SU), or with MDSCs loaded with NP conjugated to E6E7 and PGN (NP- E6E7PGN), or with MDSCs loaded with NP conjugated to E6E7 and PGN and additionally treated with SU (NP-E6E7PGN+SU).
Figure 25:
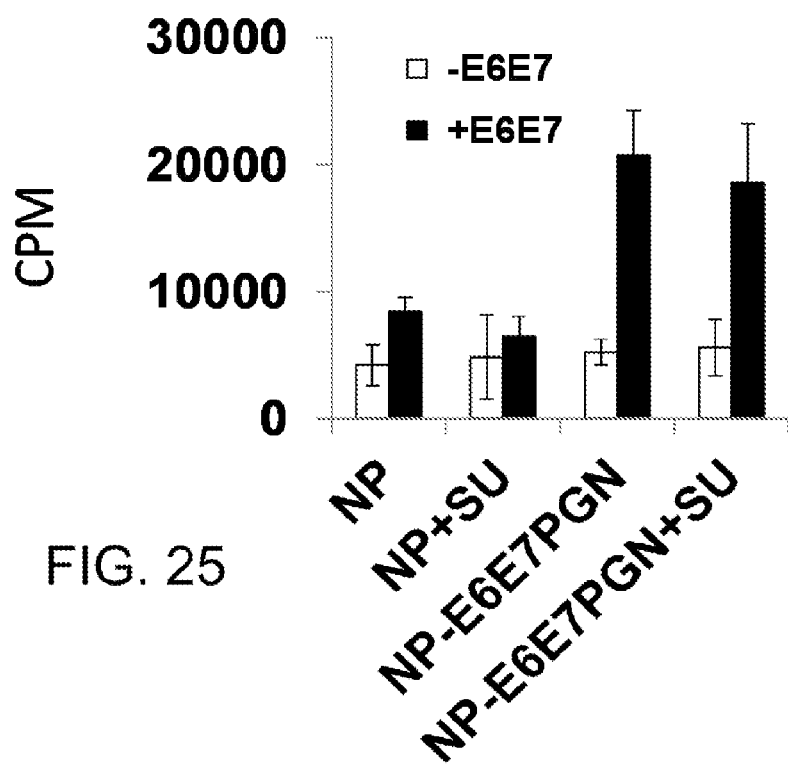
FIG. 25 is a bar graph quantifying proliferation (CPM) of Thy1.2 T cells purified from spleens of vaccinated mice after MDSC adoptive transfer for 14 days in response to E6/E7 peptides (+E6E7) or absence of E6/E7 peptides (−E6E7) in the presence of antigen presenting cells. The groups from which the T cells were isolated are indicated and as described above for FIG. 24.

The MDSC-nanoparticle immunization protocol using native tumor associate antigens (E6/E7 antigens) was evaluated in the TC-1 metastatic cervical carcinoma model. TC-1 tumor cells were inoculated intra venues in syngeneic C57BL/6 mice ($3 \times 10^5$ TC-1 cells/mouse) for 10 days to develop lung metastases. MDSCs were harvested from tumor-bearing mice and were divided randomly into 4 groups: NP (empty nanoparticle carrier); nanoparticle (NP); combination of NP-loaded MDSC and sunitinib malate treatment (NP+SU); nanoparticle conjugated with E6/E7 and PGN (NP-E6E7-PGN); combination of NP-E6E7-PGN-loaded MDSC and sunitinib malate treatment (NP-E6E7-PGN+SU) (n=3-7/group). MDSCs were cultured overnight in the indicated conditions and MDSCs ($5 \times 10^6$/mouse) were adoptively transferred into recipient mice. Sunitinib malate treatment was continuously given (0.015 mg/mice/day). Mice that received MDSCs loaded with NP-E6E7-PGN in combination with sunitinib malate treatment had significantly ($p<0.01$) improved survival compared to mice that received MDSCs loaded with NP-E6/E7-PGN without sunitinib malate in the context of this E6/E7 positive metastatic tumor model (FIG. 24). T cells isolated from the spleen exhibited significant levels of proliferation when stimulated with E6/E7 peptides in vitro (FIG. 25) and direct cytolytic activity against parental tumor cells of F4/80+ macrophages (FIG. 26A) and T cells (FIG. 26B) isolated from tumor infiltrating leukocytes was observed. These results indicate that MDSC loaded NP+PGN+E6/E7 antigen in the presence of sunitinib malate can induce the strongest direct T cell cytolytic activity against E6/E7 expressing parental tumor cells, modulate the tumor microenvironment and generate M1 like functional macrophage to mediated direct tumor killing.

Example 13

Figure 27A:
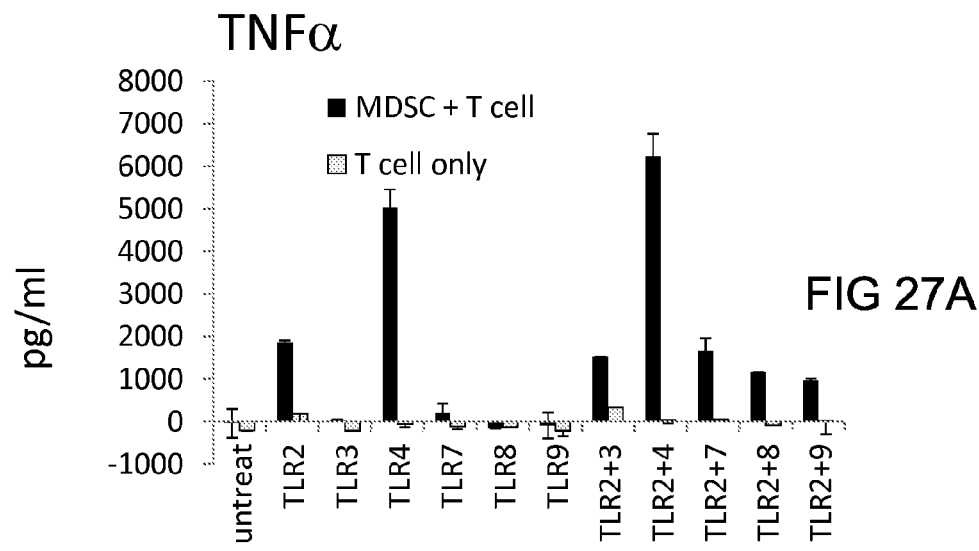
FIGS. 27A, 27B and 27C are bar graphs showing levels of TFNa, IL-17 and IFNγ in the culture supernatants of OTH transgenic T cells incubated in the presence (MDSC+ T cell, black bar) or absence (T cell only, gray bar) of MDSCs and pulsed with peptide antigen.
Figure 27B:
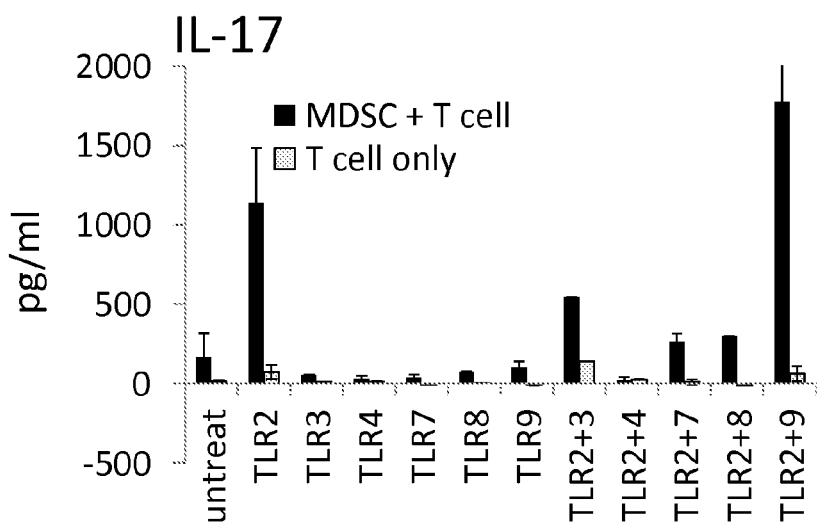
Figure 27C:
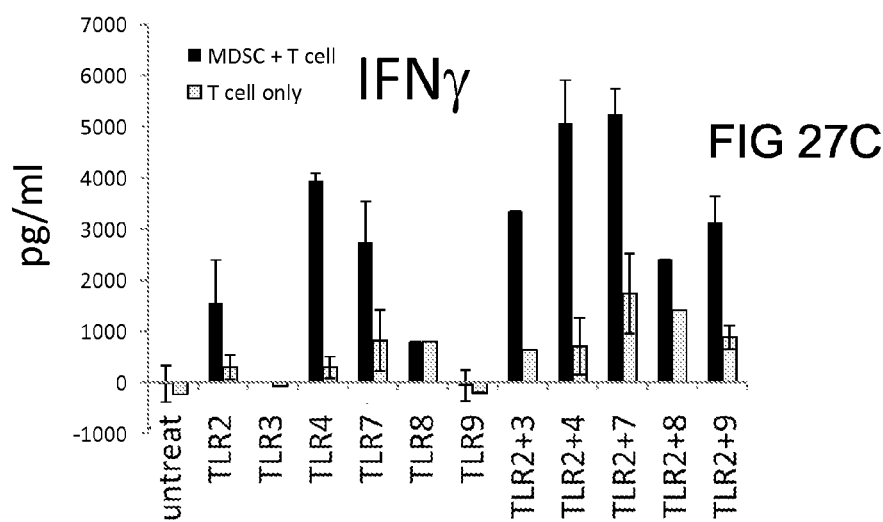

Effect of Combined Toll-Like Receptor Ligands on MDSC Mediated T Cell Activation This Example demonstrates that MDSCs treated with TLR ligands, and in particular, with combinations of TLR ligands, induce T cells to secrete increased levels of the pro-inflammatory cytokines TNF-alpha (α), IL-17 and IFNγ, compared to single TLR ligands. Naïve OTII CD4 T cells isolated from spleen of OVA TCR transgenic mice C57BL/6 mice were cultured with OVA peptide in the presence or absence of MDSCs previously incubated in the presence of the indicated TLR ligands or combinations thereof. As shown in FIG. 27, the combination of ligands for TLR2+4 (PGN+LPS) induced high levels of TNF-alpha and IFNγ. The combination of TLR2+9 (PGN+CpG) induced high levels of IL-17 and IFNγ. Thus, combinations of TLR ligands have a synergistic effect on the ability of MDSCs to activate T cells.

Discussion

Over the past several years, cell-mediated delivery of tumor specific therapies has become a topic of much interest. For a cell to be considered for this type of therapy it must exhibit several characteristics: the cell must be able to take up the treatment and without dying, it must be able to deliver the therapy directly to the tumor, promoting effective tumor killing, and it must not have deleterious systemic or protumor side effects. As demonstrated herein, MDSCs prove to be an excellent candidate that meets those criteria.

It is demonstrated herein that MDSCs exhibit very strong tumor tropism. Further, MDSCs can be labeled magnetically and fluorescently, and their migration followed in tumor-bearing hosts, thus making it possible to use them for diagnostic and imaging purposes. It is also demonstrated herein that MDSCs leave the circulation and, by 48 hours post-transfer, start accumulating within tumors, peaking at 72 hours post-transfer. However, the presence of labeled cells within the tumor can still be seen for up to a week after transfer. MDSCs accumulate at the tumor periphery as well as perivascularly. The presence in the perivascular region is likely due to the fact that MDSCs are carried to the tumor via the vasculature, however it may also be indicative of their role in angiogenesis, which has been reported.

Ferumoxides labeling offers advantages over immunologic labeling techniques, including the ability to follow migration longitudinally in the same individual in vivo, which can translate well to humans. Cells require little ferumoxides for MRI identification, and very few cells need to be present for detection by MRI. It has previously been shown that a single SPIO-labeled cell can be identified in vivo via MRI. However, reliable results have been achieved at detecting 125 cells when identifying dendritic cells, which are similar in size to MDSCs, and appear to take up ferumoxides similarly. Due to its dextran coat, ferumoxides remains intact and detectable longer than fluorescent labeling and its presence can be confirmed via ICP-MS, relaxometry, and histology. Ferumoxides is also nontoxic and has been approved by the FDA for use in humans.

The challenges presented in effective VSV therapy make it very useful in demonstrating how MDSCs can improve current tumor therapies. VSV inhibits tumor growth and prolongs survival in tumor-bearing mice. VSV is typically injected intratumorally or intrahepatically to achieve this response. There are no reports of systemic infusion of VSV promoting robust anti-tumor responses or long-term survival in vivo. Systemically administered therapy offers advantages over intratumoral administration: it enables avoidance of post surgical complications and can reach locations that would otherwise not be accessible surgically. In 2008, there were over 1,450,000 new cancer cases diagnosed in the United States, and 570,000 deaths attributed to the disease. The majority of these deaths were due to metastatic spread of the disease, not primary tumor growth. MDSCs migrate to locations where inflammatory mediators are present, such as sites of metastases. Therefore, MDSC therapy as provided herein can lead to the eradication of metastatic lesions which have yet to be identified.

VSV therapy presents several unique challenges which MDSC-therapy, as well as use of the second generation, VSV (M3) mutant, attempt to overcome Immune competent hosts are able to mount a rapid cellular immune response that halts viral replication after a few days. The oncolytic potency of VSV can be enhanced through vector-mediated inhibition of NK and NKT cells [Altomonte et al. (2009) Cancer Gene Ther. 16(3): 266-278]. By employing the VSV(M3) mutant, which has an altered matrix protein and expresses the murine gammaherpesvirus M3 protein, the virus replicates longer and results in a more potent oncolytic response [Wu, 2008 supra]. Unfortunately, VSV also harbors the risk of neuropathy, including paralysis or lethal encephalitis. What is intriguing with the treatment regimens disclosed herein is that none of the mice treated with VSV-MDSCs suffered from such effects. It was also confirmed histologically as well as through $TCID_{50}$ that the central nervous system of mice treated with VSV-MDSCs is relatively spared from VSV infection. Further by targeting the virus directly to the tumor using the MDSC according to the present invention, the pharmacologic dose can be reduced, thus increasing the therapeutic index.

While VSV can be passively associated with mammalian cells, it does so at a low copy number, making it preferable to have alternate methods of virus loading on MDSCs. To this end an antibody against the VSV-G surface protein can be used. This antibody is non-neutralizing and bound by the high affinity FcγRI found on all monocytic cells. It was demonstrated herein that this antibody can be used to increase the amount of virus bound to and ultimately delivered by MDSCs. Finally, when combining both the second-generation virus and antibody conjugation long-term survival within a cohort of tumor-bearing mice was demonstrated. This improved survival is attributable to a combination of increased viral concentration within the tumor as well as avoidance of cellular antiviral responses.

Previously Macrophages, T-cells, and NK cells have been employed as vectors for tumor-specific delivery of VSV. These methods have numerous drawbacks. Tumor specific T-cells are notoriously challenging to isolate from nonexperimental models such as in the OT-II model which has been previously used. Both NK cells and T-cells are significantly smaller than MDSCs and are not phagocytic, limiting both the quantity and the methods with which they can take up OVs. Neither cell possesses the high affinity FcγR that MDSCs possess, which was employed here to increase the viral loading. Macrophages, which are large and phagocytic, lack the tumor specificity discovered here for MDSCs. In fact all of the tested cell types lack the tumor tropism inherent in MDSCs.

Another advantage to MDSC therapy is that it need not be limited to VSV. There are numerous other oncolytic viruses that offer advantages depending on tumor type.

Currently there are multiple studies underway involving nanoparticles bearing therapeutic agents, including chemotherapeutic drugs and siRNA, all of which could be loaded onto MDSCs. As demonstrated herein, MDSCs can efficiently transport nanoparticles to tumor sites and are effective for tumor killing. In particular, nanoparticles conjugated to TLR ligands (PGN) or tumor-associated antigens (E6E7 peptide) were effectively delivered to tumor sites by MDSCs and increased survival rates in tumor bearing mice. By targeting treatments specifically to tumors, higher intratumoral concentrations of therapeutic agents are advantageously achieved, while keeping the systemic doses low. Moreover, combination treatment with sunitinib malate was particularly effective.

While MDSCs have gained notoriety for their protumor qualities, it has been previously demonstrated that their phenotype is plastic, and that under various conditions, MDSCs can exhibit an anti-tumor, M-1 like phenotype. Indeed, it is demonstrated herein that while naïve MDSCs are M2-like, when exposed to virus, the cells are primed towards M1, upregulating iNOS, downregulating Arg, and actively killing tumor cells. This unique quality of MDSCs makes them an excellent candidate for cell-mediated therapies.

The identification of universal epitopes for the classification of human MDSCs has proven more challenging than for murine MDSCs, however, progress is being made toward finding a unified phenotype across a variety of cancer patients. See, Mandruzzato, S. et al. *J Immunol* 182, 6562-6568 (2009); Hoechst, B. et al. *Hepatology* 50, 799-807 (2009); Rodriguez, P. C. et al. Cancer Res 69, 1553-1560 (2009); Liu, C. Y. et al. *J Cancer Res Clin Oncol* (2009). Based on the discoveries presented herein, MDSCs, which could be generated from the blood or bone marrow of cancer patients, can be armed with cancer-specific therapies, and transferred back to the patient therapeutically. Such therapeutic methods may be particularly helpful for treatments that have a low threshold for systemic toxicity.

In humans, and in mice, MDSCs have been found to increase in virtually every form of cancer, including colon, renal cell, breast cancer, melanoma, and hepatocellular carcinoma (HCC). In MDSCs, the immune system has provided an excellent vector for targeting therapeutics, a Trojan horse to be exploited in treating cancer and possibly treating a variety of other diseases.

* * *

It is to be understood that the invention is not limited only to the specific types of tumor exemplified herein. The present methods and compositions are effective for targeting anti-tumor agents, such as oncolytic viruses, chemotherapeutic drugs and other small molecules to any tumor.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A composition comprising an isolated myeloid derived suppressor cell (MDSC) loaded with an oncolytic virus.

2. The composition according to claim 1, wherein the oncolytic virus is a member selected from the group consisting of vesicular stomatitis virus (VSV), rVSV(MA51)-M3 mutant VSV, Ad1TRAIL-EI, ONYX-015, CV706, JX-584, CGTG-102, vaccinia virus, reovirus, and poliovirus.

3. The composition according to claim 1, wherein the MDSC is infected with the oncolytic virus.

4. The composition according to claim 1, wherein the MDSC is conjugated to the oncolytic virus.

5. A composition comprising an isolated MDSC loaded with an oncolytic VSV.

6. A pharmaceutical formulation comprising a MDSC loaded with an oncolytic virus, and a pharmaceutically acceptable carrier.

7. The pharmaceutical formulation according to claim 6, wherein the formulation is formulated for parenteral administration.

8. A method for treating a tumor comprising administering to a patient in need of such treatment an effective amount of a composition comprising an isolated MDSC loaded with an oncolytic virus.

9. The method according to claim 8 wherein the patient is a mammal.

10. The method according to claim 9, wherein the mammal is a human.

11. The method according to claim 8, wherein the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, meduUoblastoma, craniopharyngioma, ependymoma, pinealoma, hemangioblastoma, acoustic neuroma, oligodendroglioma, meningioma, melanoma, neuroblastoma, and retinoblastoma.

12. The composition according to claim 1, wherein the MDSC expresses the cell surface markers CD1 lb and CD33.

13. The composition according to claim 12, wherein the MDSC also expresses at least one cell surface marker selected from the group consisting of CD 14, CD 15, CD 16, CCR2, CCR7 and CD34.

14. The method according to claim 8, wherein the MDSC expresses the cell surface markers CD 1 lb and CD33.

15. The method according to claim 14, wherein the MDSC also expresses at least one cell surface marker selected from the group consisting of CD14, CD15, CD16, CCR2, CCR7 and CD34.

16. The composition according to claim 1, wherein the MDSC expresses the cell surface markers CD1 lb, CD1 15, Grl and Ly6C.

17. The method according to claim 8, wherein the MDSC expresses the cell surface markers CD11b, CD115, Gr1, CCR7, CCR2 and Ly6C.

\* \* \* \* \*